United States Patent
Nelson et al.

(10) Patent No.: US 11,848,817 B2
(45) Date of Patent: Dec. 19, 2023

(54) TECHNIQUES FOR UPDATING EDGE DEVICES

(71) Applicant: Oracle International Corporation, Redwood Shores, CA (US)

(72) Inventors: Jonathon David Nelson, Verona, WI (US); David Dale Becker, Seattle, WA (US)

(73) Assignee: ORACLE INTERNATIONAL CORPORATION, Redwood Shores, CA (US)

( * ) Notice: Subject to any disclaimer, the term of this patent is extended or adjusted under 35 U.S.C. 154(b) by 0 days.

(21) Appl. No.: 17/589,360

(22) Filed: Jan. 31, 2022

(65) Prior Publication Data

US 2022/0326941 A1    Oct. 13, 2022

Related U.S. Application Data

(60) Provisional application No. 63/173,244, filed on Apr. 9, 2021.

(51) Int. Cl.
*H04L 41/0806* (2022.01)
*H04L 67/10* (2022.01)
(Continued)

(52) U.S. Cl.
CPC ........ *H04L 41/0806* (2013.01); *G06F 3/0604* (2013.01); *G06F 3/067* (2013.01);
(Continued)

(58) Field of Classification Search
CPC ............. G06F 8/60–66; G06F 2201/84; G06F 11/1469; G06F 9/4406
(Continued)

(56) References Cited

U.S. PATENT DOCUMENTS

| 8,301,720 B1 | 10/2012 | Thakker et al. |
| 10,656,865 B1 | 5/2020 | Janse van Rensburg et al. |

(Continued)

FOREIGN PATENT DOCUMENTS

| EP | 2369782 | 9/2011 |
| EP | 3391588 | 10/2018 |

(Continued)

OTHER PUBLICATIONS

Edge computing, Wikipedia, 2021, 5 pages, [retrieved on Aug. 1, 2023], Retrieved from the Internet: <URL:https://web.archive.org/web/20210112031346/https://en.wikipedia.org/wiki/Edge_computing>.*

(Continued)

*Primary Examiner* — Geoffrey R St Leger
(74) *Attorney, Agent, or Firm* — Kilpatrick Townsend & Stockton LLP

(57) ABSTRACT

Techniques discussed herein relate to updating an edge device (e.g., a computing device distinct from and operating remotely with respect to a data center). The edge device can execute a first operating system (OS). A manifest specifying files of a second OS to be provisioned to the edge device may be obtained. The manifest may further specify a set of services to be provisioned at the edge device. One or more data files corresponding to a difference between a first set of data files associated with the first OS and a second set of data files associated with the second OS may be identified. A snapshot of the first OS may be generated, modified, and stored in memory of the edge device to configure the edge device with the second OS. The booting order of the edge device may be modified to boot utilizing the second OS.

20 Claims, 12 Drawing Sheets

(51) Int. Cl.

| | |
|---|---|
| *G06F 8/658* | (2018.01) |
| *G06F 8/61* | (2018.01) |
| *G06F 9/4401* | (2018.01) |
| *G06F 11/14* | (2006.01) |
| *H04L 12/46* | (2006.01) |
| *G06F 3/06* | (2006.01) |
| *H04L 9/40* | (2022.01) |
| *G06F 9/455* | (2018.01) |
| *G06F 9/50* | (2006.01) |
| *H04L 9/08* | (2006.01) |

(52) U.S. Cl.
CPC .......... *G06F 3/0622* (2013.01); *G06F 3/0655* (2013.01); *G06F 3/0659* (2013.01); *G06F 3/0679* (2013.01); *G06F 8/61* (2013.01); *G06F 8/658* (2018.02); *G06F 9/4406* (2013.01); *G06F 9/45558* (2013.01); *G06F 9/505* (2013.01); *G06F 9/5055* (2013.01); *G06F 9/5077* (2013.01); *G06F 9/5088* (2013.01); *G06F 11/1451* (2013.01); *G06F 11/1469* (2013.01); *H04L 9/0897* (2013.01); *H04L 12/4641* (2013.01); *H04L 63/0471* (2013.01); *H04L 63/0478* (2013.01); *H04L 63/0485* (2013.01); *H04L 63/06* (2013.01); *H04L 63/0876* (2013.01); *H04L 63/162* (2013.01); *H04L 63/20* (2013.01); *H04L 67/10* (2013.01); *G06F 2009/45562* (2013.01); *G06F 2009/45587* (2013.01); *G06F 2009/45595* (2013.01); *G06F 2201/84* (2013.01)

(58) Field of Classification Search
USPC .................................................. 717/168–178
See application file for complete search history.

(56) References Cited

U.S. PATENT DOCUMENTS

| | | | |
|---|---|---|---|
| 10,785,211 B2 | 9/2020 | Zhu et al. | |
| 10,911,558 B1 | 2/2021 | Witzel | |
| 10,991,558 B2 | 4/2021 | Bern et al. | |
| 11,044,118 B1 | 6/2021 | Reed et al. | |
| 11,188,376 B1 | 11/2021 | Alexander et al. | |
| 11,191,013 B1 | 11/2021 | Kalkunte et al. | |
| 11,281,857 B1 | 3/2022 | Craft et al. | |
| 11,349,710 B1 | 5/2022 | Nelson et al. | |
| 2004/0252717 A1 | 12/2004 | Solomon et al. | |
| 2010/0228919 A1* | 9/2010 | Stabrawa ............ | G06F 12/0866 711/120 |
| 2012/0066680 A1* | 3/2012 | Amano ............... | G06F 9/45533 718/1 |
| 2018/0054354 A1 | 2/2018 | Wienstroer et al. | |
| 2018/0069804 A1 | 3/2018 | Laplanche et al. | |
| 2019/0138294 A1 | 5/2019 | Smith et al. | |
| 2019/0347121 A1* | 11/2019 | Luo ..................... | G06F 9/542 |
| 2020/0007414 A1 | 1/2020 | Smith et al. | |
| 2020/0026524 A1* | 1/2020 | Roland ................ | G06F 3/0617 |
| 2020/0097274 A1 | 3/2020 | Sarkar et al. | |
| 2020/0213227 A1 | 7/2020 | Pianigiani et al. | |
| 2020/0293347 A1* | 9/2020 | Buckley .............. | G06F 9/4451 |
| 2020/0351323 A1 | 11/2020 | Gong et al. | |
| 2021/0112034 A1 | 4/2021 | Sundararajan et al. | |
| 2021/0117134 A1 | 4/2021 | Keys et al. | |
| 2021/0314365 A1 | 10/2021 | Smith et al. | |
| 2022/0334725 A1 | 10/2022 | Mertes et al. | |

FOREIGN PATENT DOCUMENTS

| | | |
|---|---|---|
| WO | 2016069638 | 5/2016 |
| WO | 2019236181 | 12/2019 |
| WO | 2020052322 | 3/2020 |

OTHER PUBLICATIONS

AWS Snowball Edge Developer Guide AWS Snowball Edge, Available Online at: https://docs.aws.amazon.com/snowball/latest/developer-guide/AWSSnowball-dg.pdf#UsingCluster, 2021, 227 pages.

Cisco SD-WAN Design Guide, Available Online at: https://www.cisco.com/c/en/us/td/docs/solutions/CVD/SDWAN/cisco-sdwan-design-guide.html, Sep. 2020, 102 pages.

Device Update APT Manifest, Available Online at: https://docs.microsoft.com/en-us/azure/iot-hub-device-update/device-update-apt-manifest, Feb. 17, 2021, 2 pages.

Encrypting Traffic Between Nodes with IPsec, Available Online at: https://docs.openshift.com/container-platform/3.11/admin_guide/ipsec.html, Accessed from Internet on May 21, 2021, 8 pages.

NSX-T Data Center, Available Online at: https://docs.vmware.com/en/VMware-NSX-T-Data-Center/2.5/nsxt_25_install.pdf, Jul. 31, 2020, 276 pages.

Software Installation and Upgrade for vEdge Routers, Available Online at: https://www.cisco.com/c/en/us/td/docs/routers/sdwan/configuration/sdwan-xe-gs-book/hardware-and-software-installation.html, 2021, 2 pages.

Upgrade an Edge Cluster, Available Online at: https://partners-intl.aliyun.com/help/doc-detail/154532.htm, 2021, 4 pages.

Upgrade NSX Edge Cluster, Available Online at: https://docs.vmware.com/en/VMware-NSX-T-Data-Center/3.1/nsxt_31_upgrade.pdf, 2021, pp. 1-57.

Akesson et al., How to Build a Resilient Over-the-Air Update Solution, Available Online at: https://techcommunity.microsoft.com/t5/internet-of-things/how-to-build-a-resilient-over-the-air-update-solution/ba-p/2163991, Mar. 2, 2021, 4 pages.

Asif et al., Prototype Implementation of Edge Encryption in IoT Architecture, 10th International Conference on Computing, Communication and Networking Technologies, Jul. 6-8, 2019, 7 pages.

Pavlik, Managing Thousands of Edge Kubernetes Clusters with GitOps, Available Online at: https://www.volterra.io/resources/blog/managing-thousands-of-edge-kubernetes-clusters-with-gitops, Dec. 18, 2019, 8 pages.

U.S. Appl. No. 17/733,602, Notice of Allowance dated Nov. 25, 2022, 17 pages.

International Application No. PCT/US2022/023549, International Search Report and Written Opinion dated Jun. 22, 2022, 12 pages.

Villari et al., Deployment Orchestration of Microservices with Geographical Constraints for Edge Computing, 2017 IEEE Symposium on Computers and Communications, Jul. 3, 2017, pp. 633-638.

Villari et al., Osmotic Computing: A New Paradigm for Edge/Cloud Integration, IEEE Cloud Computing, vol. 3, No. 6, Dec. 30, 2016, pp. 76-83.

U.S. Appl. No. 17/531,632, Notice of Allowance dated Apr. 15, 2022, 19 pages.

* cited by examiner

TECHNIQUES FOR UPDATING EDGE DEVICES

CROSS-REFERENCE TO RELATED APPLICATIONS

This non-provisional application claims priority to U.S. Patent Application No. 63/173,244, filed on Apr. 9, 2021, entitled "Cloud Computing Edge Computing Device (Rover)," the disclosure of which is herein incorporated by reference in its entirety for all purposes.

BACKGROUND

In cloud computing, processing and storage is generally performed by one or more service providers implemented at a centralized location. Data can be received from customers at the centralized location, processed there, and then the processed (or other) data can be transmitted back to customers. However, having a centralized location for cloud infrastructure components may not be ideal in various scenarios. For example, when there are hundreds or thousands of Internet of Things (IoT) devices transmitting data to the central servers, and especially when those IoT devices are not geographically close to the cloud infrastructure computing devices, conventional centralized systems are not ideal. These IoT devices may be considered on the "edge," as in they are not close to the central servers.

Additionally, there may be other instances when the centralized location for cloud components is less than ideal. For example, if the data is collected (e.g., by IoT devices) in a disconnected region or a location with no Internet connectivity (e.g., remote locations). Current centralized cloud computing environments may not meet time sensitivity requirements when streaming data due to the inherent latency of their wide-area network connections. Remotely generated data may need to be processed more quickly (e.g., to detect anomalies) than conventional centralized cloud computing systems allow. Thus, there are challenges with managing a traditional cloud computing environment that relies on centralized components. For example, a centralized workflow manager may be suboptimal for managing workflows at geographically remote devices.

BRIEF SUMMARY

Techniques are provided (e.g., a method, a system, non-transitory computer-readable medium storing code or instructions executable by one or more processors) for updating an edge device (e.g., a computing device configured to deliver computing and storage at remote locations separate from the centralized data center and lacking a public/private network connection). Various embodiments are described herein, including methods, systems, non-transitory computer-readable storage media storing programs, code, or instructions executable by one or more processors, and the like.

One embodiment is directed to a method for updating an edge device. The method may comprise executing, by an edge device, a first operating system, the edge device being configured to selectively execute within an isolated computing environment. The method may further comprise receiving, by the edge device, a request for a second operating system to be provisioned to the edge device. In some embodiments, the request may include one or more files of the second operating system and/or a manifest that identifies one or more files of the second operating system. The method may further comprise generating, by the edge device, a snapshot of the first operating system. The method may further comprise identifying one or more data files that correspond to a difference between a first set of data files associated with the first operating system and a second set of data files associated with the second operating system. The method may further comprise storing the snapshot of the first operating system within memory of the edge device. The method may further comprise configuring the edge device with the second operating system based on modifying the snapshot to comprise the one or more data files that correspond to the difference between the first set of data files and the second set of data files. The method may further comprise modifying a booting order of the edge device to configure the edge device to execute the second operating system. The operations of this method may be performed in any suitable order.

In some embodiments, the method further comprises maintaining data (e.g., one or more snapshots and/or records) that indicates the first set of data files correspond to the first operating system and the second set of data files corresponds to the second operating system. In some embodiments, at least one data file is common between the one or more data files and the second set of data files.

A manifest may be included with the request. The manifest may specify, among other things, a set of services to be provisioned at the edge device where the edge device initially comprises a set of previously-provisioned services. In these embodiments, the set of previously-provisioned services may be compared to the set of services specified by the manifest. One or more services that correspond to a difference between the set of previously-provisioned services and the set of services specified by the manifest may be identified. One or more image containers corresponding to the one or more services may be obtained from a data store of the edge device (or may be included in the request). One or more tasks associated with provisioning one or more services at the edge device may be executed in accordance with the manifest. An additional indication may be maintained in a record (e.g., a snapshot, a data record, or the like), indicating that a first set of image containers corresponding to the set of previously-provisioned services correspond to a first configuration of the edge device and that a second set of image containers corresponds to a configuration of the edge device specified by the manifest.

In some embodiments, the local memory (e.g., one or more memories of the edge device) stores only one instance of a data resource (e.g., a file, a given image container, etc.). The edge device may be configured with a computer storage format that comprises a file system that implements a copy-on-write protocol.

In some embodiments, a rollback option that enables a user to roll back from the second operating system to the first operating system is provided. The rollback option may be automatically executed when an indication that the second operating system is approved has not been received in a threshold period of time since the second operating system has been in use.

In some embodiments, an edge device is disclosed. The edge device may operate alone, or as part of a computing cluster of a plurality of edge devices. In some embodiments, the edge device comprises one or more processors and one or more (non-transitory) memories configured with computer-executable instructions that, when executed by the one or more processors, cause the edge device to perform the method disclosed above.

Some embodiments disclose a non-transitory computer-readable storage medium comprising computer-executable instructions that, when executed with one or more processors of an edge device (e.g., an edge device operating as part of a computing cluster of edge devices), cause the edge device to perform the method disclosed above.

DETAILED DESCRIPTION

Figure 1:
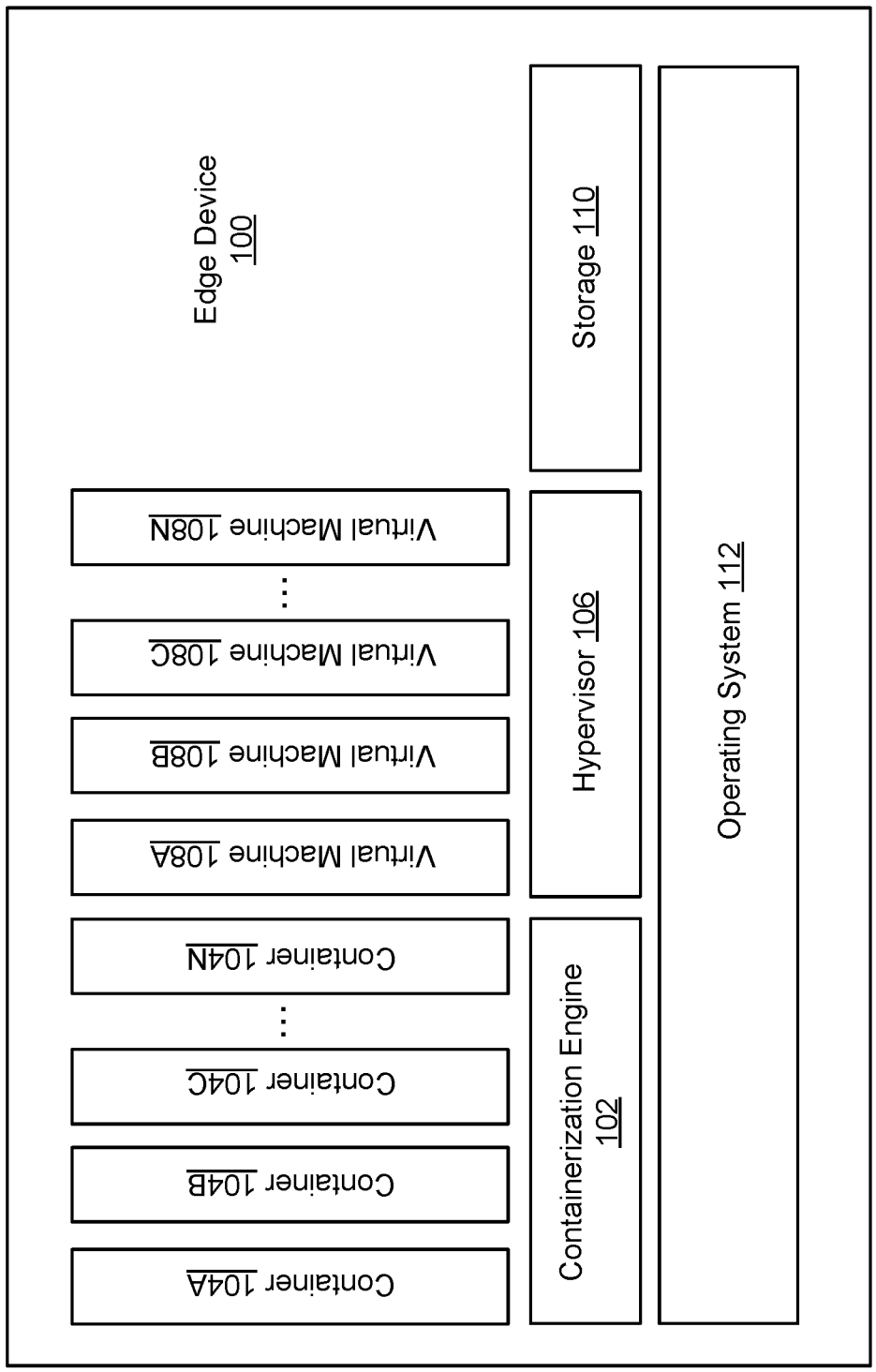
FIG. 1 is a block diagram of an example high-level architecture for a cloud infrastructure edge computing device, according to at least one embodiment.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

INTRODUCTION

In some examples, a cloud-integrated edge service (e.g., implemented in an edge computing device, also referred to as "an edge device," for brevity) may be integral in addressing the desire to run time-sensitive cloud infrastructure application outside of a centralized data center (e.g., a datacenter of a cloud infrastructure service provider). Such an edge computing device may deliver computing and storage at the edge and/or in disconnected locations (e.g., remote locations separate from the centralized data center and lacking a public/private network connection (e.g., an Internet connection, a VPN connection, a dedicated connection, etc.) to enable low-latency processing at or near the point of data generation and ingestion. In some instances, a fleet of portable (which may be ruggedized for protection) server nodes (e.g., a fleet of edge devices) may be configured to physically bring the cloud infrastructure service to remote locations where cloud technology has been considered technologically infeasible or too cost prohibitive to implement.

To a customer (e.g., a user), the edge computing device can act as an extension of their cloud infrastructure: including virtual machines (VMs), containers, functions and data files, block volumes or object store services can also be delivered from the cloud infrastructure tenancy (e.g., a tenancy of the centralized cloud computing environment) with little to no modifications, and the customer experience may remain unchanged from that of the centralized cloud computing experience. Additionally, the edge computing device may be configured to implement both a control plane and a data plane that are part of a cloud infrastructure service provider. The data plane can be configured to manage data storage, migration, processing, etc., while the control plan can be configured for controlling the various services and architecture components of the computing device. Once the edge computing device is properly connected to a customer computing device (e.g., via a local area network (LAN)), the customer may be able to utilize the IaaS service (or at least a subset of it) using the same SDK and API used with the centralized cloud service.

The edge computing device can be delivered to a customer in a pre-configured form, such that the only action that might be required of the customer is to connect the nodes to a network (e.g., a local/on premise network that is accessible by a user computing device), power them up, and/or log in. The device can be pre-configured in various ways based on customer preference/request, or it can be in one of various configurations (e.g., storage-centric, compute-centric, etc.). The node or cluster of nodes can be portable and is intended to be mobile—when moved and set up again (or used while in motion), the deployment continues to run from where it turned off (or continuously). The edge computing device can also monitor for wide area network (WAN) connection availability (e.g., the Internet or the like), and can synchronize customer and management data with the cloud once connected to a WAN.

Some potential use cases for the edge computing device include: storage and processing, compute and input/output (I/O) intensive applications, machine learning, remote computing, low latency database and analytics, and data collection and migration. More specifically, the edge device can be used for storage and processing of large volumes of images, video, audio, and IoT sensor data generated in environments where WAN connection is latent or unavailable (e.g., in remote areas, an oil off-shore platform, or the like). Once this data is pre-processed, filtered, compressed, and/or secured it may be transported or transferred to the cloud service provider, where it can be further processed by the centralized server (e.g., traditional cloud service provider). The device can also be used for compute and I/O intensive applications, where low latency is paramount, such as tactical reconnaissance or 5G communications. The device can also be used for machine learning, with models trained in the cloud and running in disconnected locations to improve efficiency, intelligence, and/or productivity in manufacturing, document management, transportation, oil and gas mining, and/or telecommunications. It can also be used for remote computing requiring elevated security and airtight containment of data. Additionally, the device can be used for low latency database and analytics workloads, with more applications optimized over time. Further, the device can also be used for data collection and migration of large sets of object and database management system (DBMS) data into a cloud service provider, e.g., at faster speeds and lower cost than a WAN transfer.

The edge device can natively support distributed cloud paradigms, where complex, multi-stage compute workflows can be separated into individual components, which in turn can be deployed to the infrastructure of the edge device, on premise, and/or in the cloud. An example of such distributed workflow is represented in the following scenario. Massive amounts of data can be collected by an edge computing node deployed on an airplane (e.g., a military jet) in a reconnaissance operation with no Internet access (e.g., a disconnected edge computing device), where this data is be pre-processed in near real time by a machine learning model previously trained by the cloud service provider that provided the edge device. Even the first pass of processing the data with the models can detect significant anomalies and can alert personnel immediately—for example, a bridge may be destroyed and therefore the troops should be rerouted. When the airplane lands, the edge computing device can be physically connected to a network (e.g., an edge station potentially deployed at the airstrip). The pre-processed, filtered, smaller dataset can be loaded for final processing to a cluster of edge computing device nodes at the edge station. The original edge computing device can be released and can be loaded on another (or the same) airplane, for example to support the next mission. When processing at the edge station is complete, a 3D map update can be issued for immediate use. Change sets can then be uploaded by the edge station cluster to a datacenter and can be used to build future models providing intelligent tactical forecasts to the reconnaissance operation, or the like.

It should be appreciated that the following techniques may be employed in a variety of contexts such as telecommunications, oil and gas, healthcare, hospitality, agriculture, transportation, and logistics, and the like.

Embodiments described herein address these and other problems, individually and collectively. Specifically, embodiments of the present disclosure provide for a cloud infrastructure edge computing device.

Edge Device Architecture

An edge computing device (sometimes referred to as "a cloud-computing edge device," a "cloud infrastructure edge computing device," or an "edge device," for brevity), extends a user's centralized cloud computing tenancy by physically putting customer infrastructure and platform services where data is generated—on the edge, on premise, or completely disconnected. Each deployment is created to address specific customer needs by provisioning VM instance images and data from the customer's centralized cloud tenancy. These workloads remain fully functional offline as the edge device adapts to the connection state, operates in harsh environmental conditions, and is ready to sync with the cloud whenever the connection is re-established.

FIG. 1 is a block diagram of an example high-level architecture for a cloud infrastructure edge computing device (e.g., edge device 100), according to at least one embodiment. An overview of the software and hardware component of the edge device 100 is provided below.

In some examples, the edge device 100 may include containerization engine 102 (e.g., Docker, Kubernetes, etc.) configured to implement one or more containers (e.g., corresponding to container(s) 104A, 104B, 104C, to 104N, collectively referred to as "container(s) 104"). A containerization engine (e.g., the containerization engine 102) may be container-orchestration system for automating computer application deployment, scaling, and management. In some embodiments, the containerization engine may be configured to provide OS-level virtualization to deliver software in packages called containers. These containers can be isolated from one another and utilize respective software, libraries, and configuration files, and can communicate with each other through well-defined channels. In some embodiments, service(s) 104 may include any suitable number of services (e.g., one or more). These services may implement at least some portion of centralized cloud capabilities. Each service may be stand-alone or operate as a distributed cluster. The edge device 100 may further include a hypervisor 106 configured to implement one or more virtual machines (e.g., virtual machines 108A, 108B, 108C, to 108N, collectively referred to as "virtual machine(s) 108" or "VMs 108").

In some examples, the edge device 100 includes storage 110 (e.g., object and/or block storage for storing local data). The edge device 100 includes operating system (OS) 112. In some embodiments, the OS 112 may be optimized for executing on an edge device and/or specific to execution on an edge device. OS 112 may be configured to manage the hardware of edge device 100 and supports a data plane of the services running on the edge device 100. The OS 112 may be configured to support a specific deployment type (e.g., a single edge device deployment, or a specific edge device cluster configuration). The OS 112 may be configured to secure the edge device by disallowing or otherwise blocking direct access by customers.

In some embodiments, the edge device 100 may include hardware such as any suitable number of central processing units (CPUs) and/or storage drives. For example, the edge device 100 depicted in FIG. 1 may have one, two, or more CPUs, with various numbers of cores per processing unit, and it may include any number of storage drives (e.g., 6.4 terabyte (TB) drives, or the like). As a non-limiting example, the edge device 100 may include block and/or object storage of any suitable size. The edge device 100 may include any suitable number of central processing units (CPUs), graphics processing units (GPUs), random access memory (RAM) of any suitable size, one or more ports (e.g., QSFP28, RJ45, dual ports, etc.), tamper-evident seals, or any suitable combination of the above components.

In some examples, the basic system functionality/services can be accessed via RESTful APIs have a custom load of software based on Linux. The virtual machine(s) 108 may individually be a Kernel-based Virtual Machines (KVM) (e.g., a virtual machine managed by a virtualization module in the Linux kernel that allows the kernel to function as a hypervisor) and/or a hardware-based Virtual Machine (e.g., a virtual machine managed by a virtualizer, such as Quick EMUlator (QEMU), that can perform hardware virtualization to enable virtual machines to emulate of number of hardware architectures). Although storage 110 is represented as a separate component from the service(s) 104 and VM(s) 108, it can run as a container (e.g., container 104A) or in a VM (e.g., VM 108A). In some examples, it may be favorable to implement the storage 110 (e.g., object storage, block storage, etc.) as a container.

Figure 2:
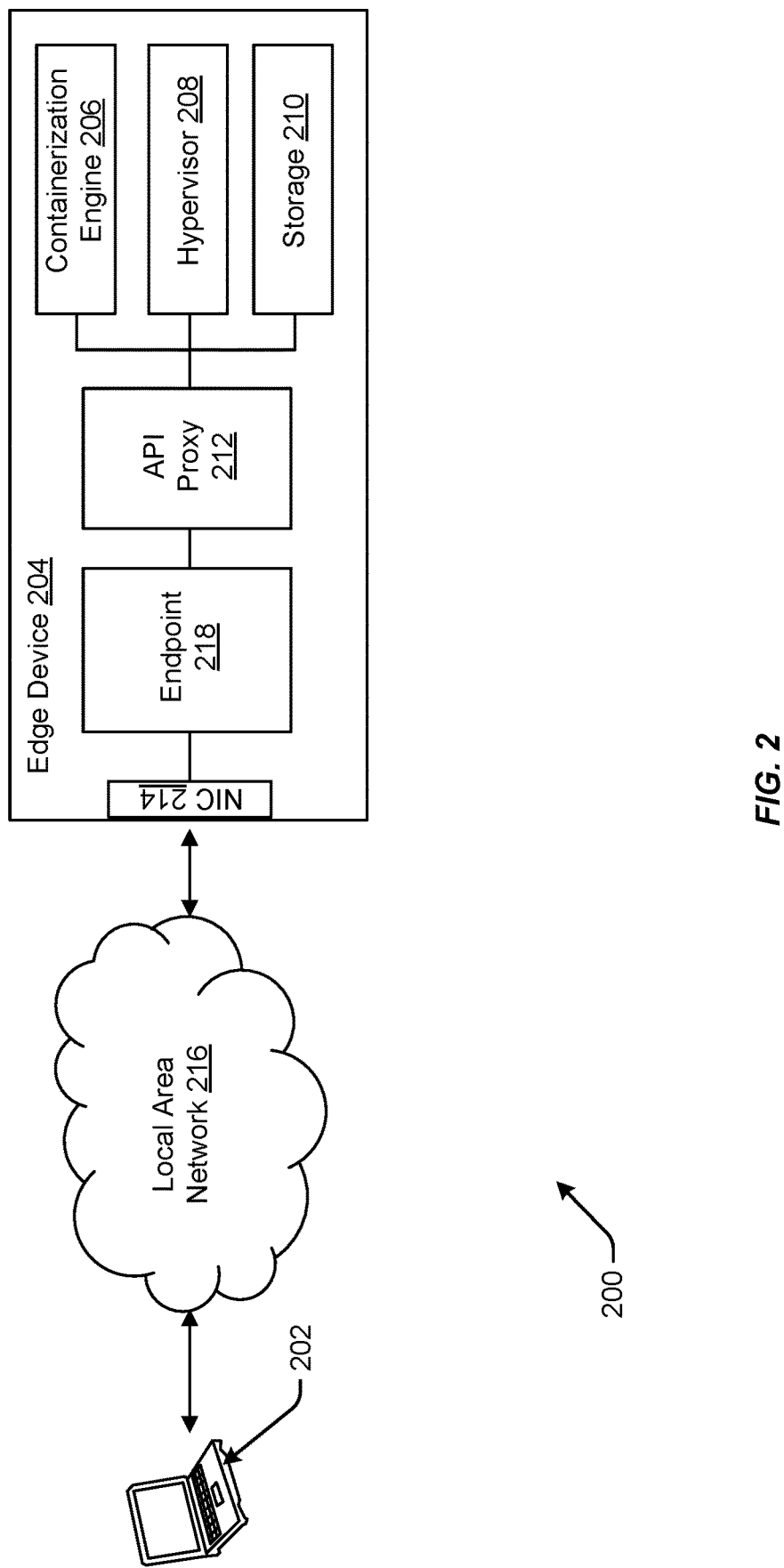
FIG. 2 is a block diagram of an example architecture for connecting a user computing device to a cloud infrastructure edge computing device, according to at least one embodiment.

FIG. 2 depicts an example architecture 200 for connecting the edge device described herein (e.g., edge device 100 from FIG. 1) to a computing device 202 (e.g., a user computing device). The computing device 202 can be any type of computing device including, but not limited to, a laptop computer, a desktop computer, or the like. The edge device 204 (an example of the edge device 100 of FIG. 1) may include containerization engine 206 (an example of the containerization engine 102 of FIG. 1), hypervisor 208 (an example of the hypervisor 106 of 1), and storage 210 (an example of the storage 110 of 1).

Additionally, as mentioned briefly above, the edge device 100 may include an API proxy 212 for managing the RESTful API calls received from the computing device 202. The API calls may enter the edge device 204 via network interface card (NIC) 214 that is internal to the edge device 204. The NIC 214 may be used to connect the edge device 204 to the computing device 202 via a local area network (e.g., the LAN 216). The API calls received by the NIC 214 may be transmitted to an exposed endpoint that may implement a Web server (e.g., endpoint 218). The web server can transmit the requests to the API proxy 212, which can route the requests to the appropriate service (e.g., containerization engine 206, hypervisor 208, and/or storage 210). The exposed endpoint/web server may also be configured to implement the lightweight console that is for use by the customer (e.g., the user interface displayed on the computing device 202).

The lightweight console can run within a web browser (e.g., Mozilla Firefox, or the like) on a laptop computer, desktop computer, or other network-accessible device (e.g., connected to the local area network (LAN 216)) that is network-connected to the edge device 204 (e.g., via a router, cable, etc.). The edge device 204 can expose the endpoint 218 for the console connection, and the web server can transmit data to the web browser of the computing device 202 over the LAN 216.

Figure 3:
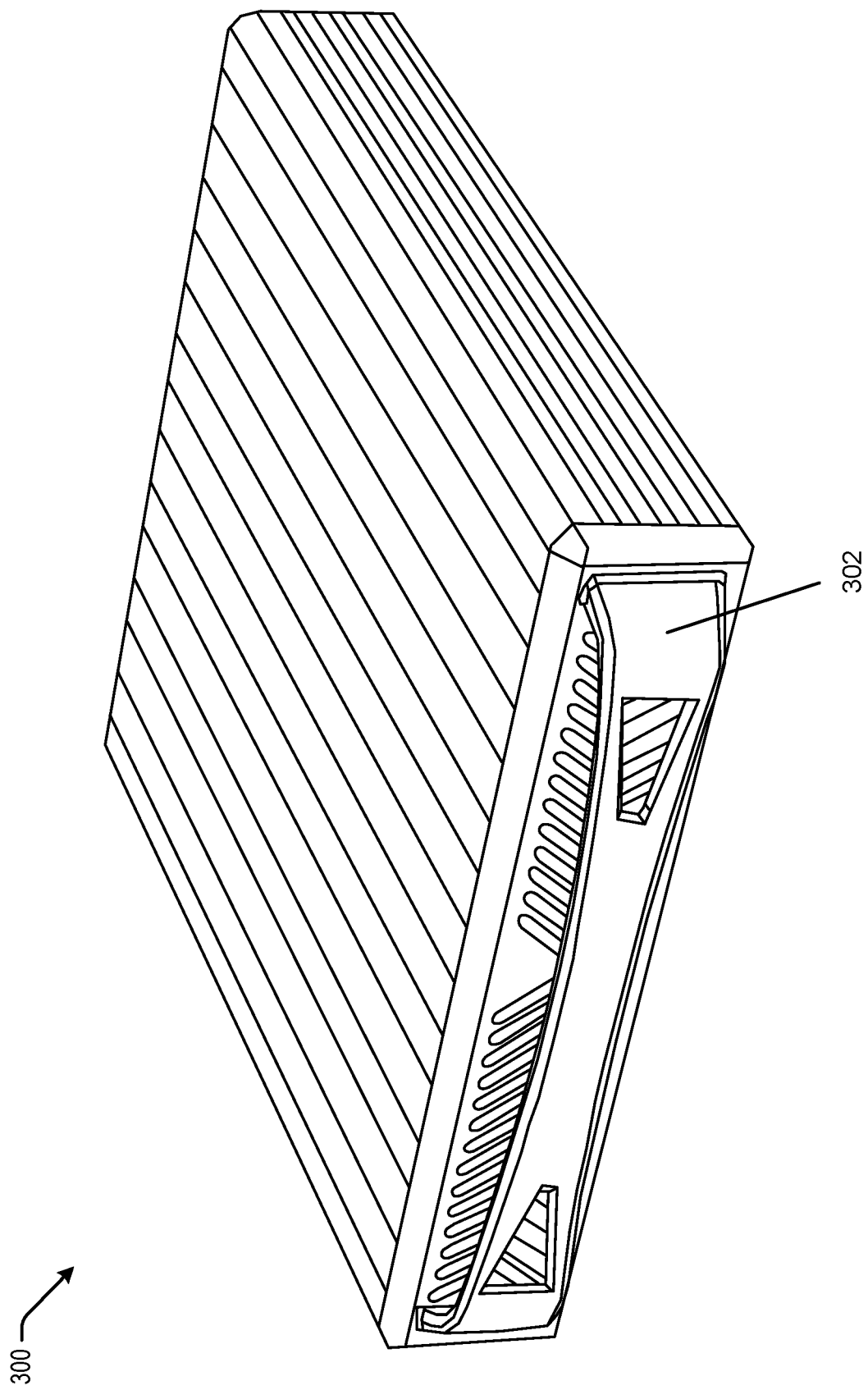
FIG. 3 is a block diagram of an example enclosure for a cloud infrastructure edge computing device, according to at least one embodiment.

FIG. 3 illustrates an example physical enclosure 300 of the edge device described herein (e.g., edge device 100 from FIG. 1). Various different form factors, shapes, colors, etc., can be employed to build a box (e.g., ruggedized) that can house the edge computing device. The physical enclosure can include handle 302, as shown, and may include tamper evident elements, so that if anyone breaks the enclosure open, it will be evident. In this way, the service provider that provides the edge computing device can ensure that the device is not modified. In some examples, the physical enclosure 300 may not be possible to open. However, in some cases, it might be possible, but it would require extreme measures.

Figure 4:
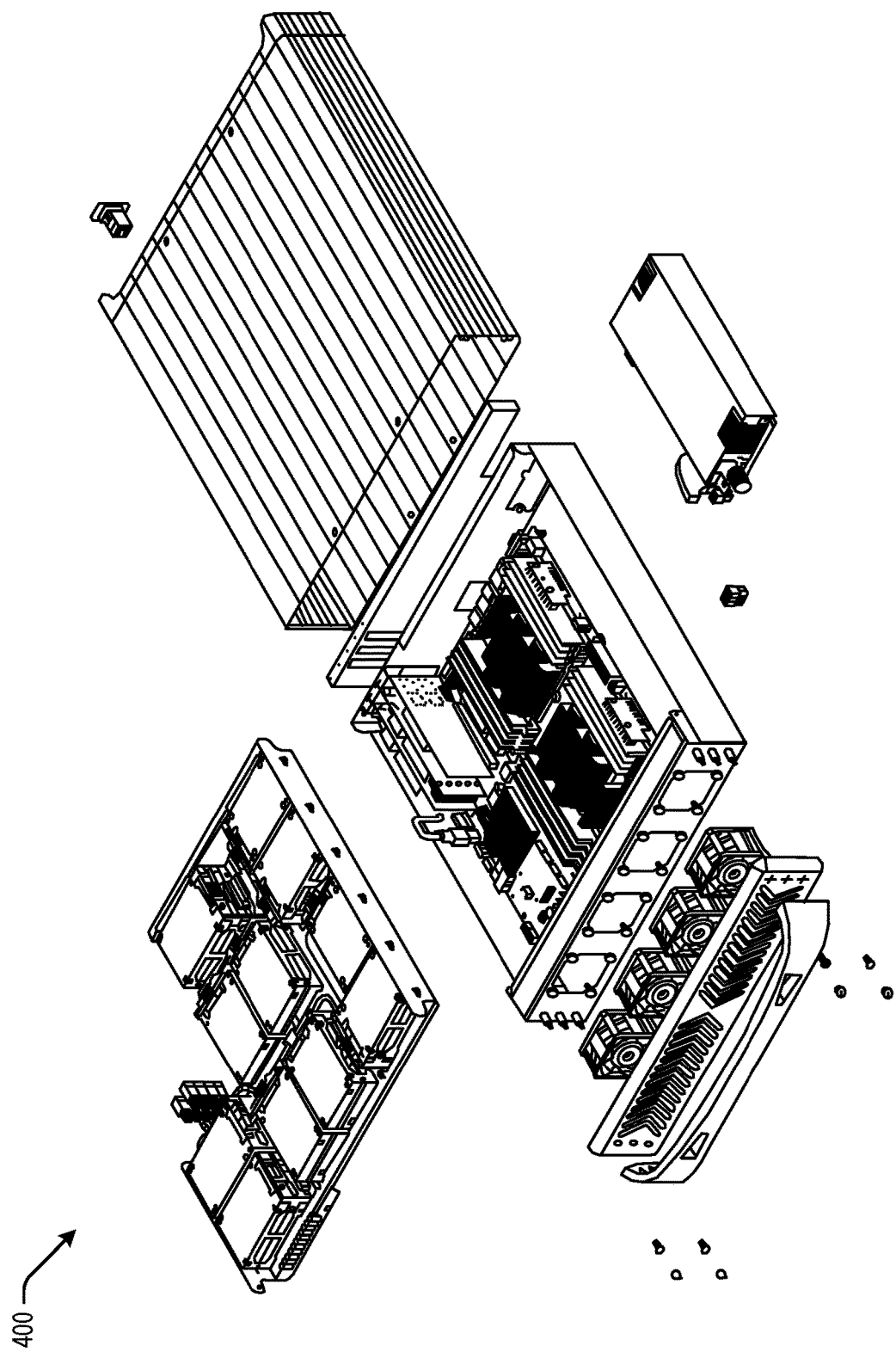
FIG. 4 illustrates an exploded view of the cloud infrastructure edge computing device described herein, in accordance with at least one embodiment.

FIG. 4 illustrates an exploded view of the cloud infrastructure edge computing device described herein (e.g., edge device 400, an example of the edge device 100 of FIG. 1), in accordance with at least one embodiment. The various components described with respect to FIGS. 1 and 2 can be communicatively attached to one or more motherboards and/or interface cards within the edge device 400. The illustrated configuration of components is but just one implementation. The specific locations of components shown is not intended to be limiting, and as noted, any configuration that is capable of implementing the functionality described herein is acceptable. Once the components are installed, the entire box can be closed, sealed, and locked with tamper-evident components.

The edge device 400 is a single enclosure. The enclosure may be designed to house any suitable number of serially attached SCSI (SAS) solid-state drives (SSDs) and all other components (e.g., CPU, memory, GPU, etc.) within the enclosure. The system may include one or more (e.g., 12 Gb) SAS connections to each drive in a fully contained sheet metal enclosure designed to fit within a standard 19" rack resting on an L bracket/shelf, on a table top or upright next to a desk with the use of a floor stand.

The system may include a tamper evident enclosure, front security plugs covering screws holding a front bezel in place with rear security interlock features. In some embodiments, the system may include a dual socket motherboard and any suitable amount of DRAM. In some embodiments, the system may include any suitable number (e.g., 2, 3, etc.) SATA SSDs, storage controllers, embedded network connections, one or more ports (e.g., dual ports, serial ports, etc.), one or more fans as part of a cooling system, or any suitable combination of the above.

As a non-limiting example, the edge device 400 may be made up of an external extruded aluminum case secured in the front with a vented bezel and rear panel only exposing I/O connections required for data transfer and management. Mounting can be designed to mount the any suitable motherboard, fans, and power supply.

Figure 5:
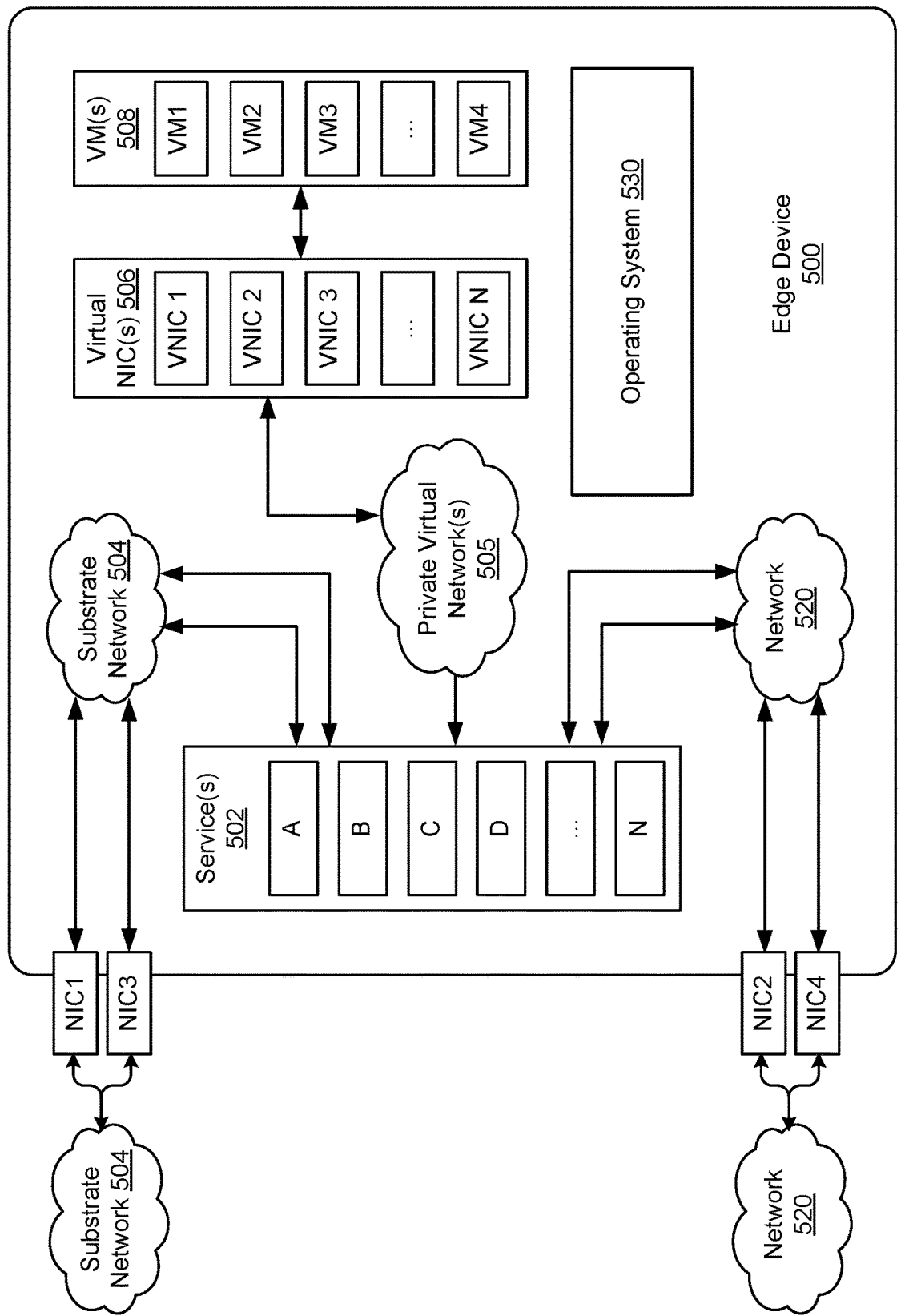
FIG. 5 is a block diagram of an example computer architecture of a cloud infrastructure edge computing device, according to at least one embodiment.

FIG. 5 is a block diagram of an example computer architecture of a cloud infrastructure edge computing device (e.g., edge device 500, an example of the edge devices 100 and 204, of FIGS. 1 and 2, respectively), according to at least one embodiment. The edge device 500 can be thought of as a cloud-integrated service that extends some or all of conventional cloud capabilities to locations that may not be accessible by or have access to cloud data centers. This can be achieved via portable ruggedized server nodes that provide cloud-like functionality in locations with no WAN connectivity. This allows customers to shift select cloud workloads to remote locations and enable intensive data processing operations close to the data ingestion points at the edge of their cloud infrastructure.

The edge device 500 may include any suitable number of services (e.g., service(s) 502). Each service may run as a container (e.g., a Docker container) locally on the edge device 500. The service(s) 502 may be communicatively connected via a substrate network 504 such that the communications between services are encrypted (e.g., in accordance with a security protocol such as MACsec). Each container may be assigned a substrate IP address (e.g., a static address) with which traffic can be addressed. In some embodiments, a security protocol (e.g., MACsec) is configured at provisioning time (e.g., before the edge device 500 is shipped to the user). The edge device's system software (including service(s) 502) may execute in the secure environments protected by boot security software (e.g., Trenchboot Secure Launch). Users may be restricted from accessing the secure environment and/or the substrate network 504. To minimize the amount of resources used by these services, the service code may be compiled and saved to disk to decrease RAM space as well as decrease the CPU load on the edge device 500.

Some example services included in service(s) 502 may include a UI console service, an identity control plane (CP) service, an identity data plane (DP) service, a compute application programming interface (API) service, a compute worker thread service, a virtual network (VN) API service, a block storage API service, a function-as-a-service service, an events service, an object storage management service (e.g., implementing a storage platform such as Ceph Storage or the like), a compute DP service (e.g., an example of hypervisor 208 of FIG. 2), a VN DP service, a block storage management service, a function-as-a-service API service, a function-as-a-service load balancing (LB) service, a function-as-a-service process thread service, a distributed data store management service (e.g., etcd3), a dynamic host configuration protocol service, a domain name system service, a network time protocol (NTP) service, to name a few. Some example functionality provided by these services is discussed below.

By way of example, compute DP service may be configured (e.g., preconfigured and provisioned onto the edge device 500) to isolate the VM(s) 508 on the same hypervisor host. The compute DP service can utilize any suitable container engine (e.g., Docker container, MicroContainer, or the like) to isolate the VM(s) 508 on the same hypervisor host from each other. The compute DP service may utilize any suitable hypervisor (e.g., Quick EMUlator (QEMU), Kernel-based Virtual Machine (KVM), etc.) to provide virtual hardware emulation for VM(s) 508. In some embodiments, VNIC(s) 506 are attached to subnets of any suitable number of virtual networks (e.g., private virtual network(s) (PVN(s))) 505 and are assigned private Internet Protocol (IP) addresses. One VM may have multiple VNICs from different VCNs and different subnets. The maximum number of VNICs can be limited by predefined thresholds (e.g., configuration data referred to as "VM shape" that defines VNICs per VM count, VNIC shape, etc.). In some embodiments, the predefined thresholds are applied to each of the VM(s) 508. The subnets utilized by the VNIC(s) 506 may be isolated by VLANs. In some embodiments, some or all of the VNIC(s) 506 may be assigned public and/or private IP addresses. A public IP address is an address in the network 520, while a private IP address refers to an IP address of the PVN(s) 505.

In some embodiments, the edge device 500 implements various networking functionality via a number of services such as a network address translation (NAT) service, a dynamic host configuration protocol (DHCP) service, a domain name system (DNS) service, a network time protocol (NTP) service, a metadata service, and a public API service). The metadata service may provide initialization data and other metadata to all VM(s) 508. In some embodiments, DHCP service assigns private IP addresses to each of the VNIC(s) 506, each of the VM(s) 508 having one or more VNICS. DNS service may provide domain name resolution to VM(s) 508 on the edge device 500. NTP may provide time synchronization to VM(s) 508. In some embodiments, a public IP service executing as part of service(s) 502 may enable a VM to access a public API without assigning the VM a public IP and without configuring a service gateway.

In some embodiments, at least one of the VM(s) 508 may implement block (or object) storage. In some embodiments, the hypervisor associated with a virtual machine may include a library that enables the hypervisor to use a distributed data storage platform (e.g., Ceph). The library may utilize a protocol associated with that storage platform (e.g., RADOS Block Device (RBD) to facilitate storage of block-based data. The distributed data storage platform may be implemented over multiple virtual machines. In some embodiments, the distributed data storage platform supports making snap shots and copying block volumes. VM images and VM block volumes can be Ceph block devices. In some embodiments, the VM(s) implementing the distributed data storage platform will use system-reserved resources (e.g., eight CPU cores, or any subset of the total number of CPUs available on the edge device 500). For example in order to provision a boot volume, a block device image may be copied to a boot volume of the block device. The distributed data storage platform may use block devices that include multiple nodes for redundancy. If some node fails then the block device can continue to operate. In some embodiments, the distributed data storage platform (e.g., Ceph or the like), automatically recovers the block device data in case of a few node failures. Block storage may be utilized to store images for any suitable deployable resource. By way of example, an image may be utilized for launching VMs. In some embodiments, the image may correspond to a particular VM shape (e.g., a compute heavy VM, a GPU optimized VM, a storage VM, and the like).

Compute API service may support the following operations: 1) VM launch and terminate, 2) VM stop, start, reboot, 3) List VMs and/or get information on a specific VM, 4) obtain VM console history API, 5) obtain a VM snap shot, 6) attach/detach block volumes, and the like. In some embodiments, Compute API service can be used to call other services (e.g., compute DP service, identity DP service for authentication and authorization, etc.).

Some of the functionality of other services will be discussed in connection with FIG. 7. In general, although each service may not be discussed in detail herein, the general functionality provided by the service(s) 502 may include the functionality of cloud services provided by a remote cloud service provider. In some embodiments, the edge device 500 may be associated with a predefined region and/or realm such that some of the service(s) 502 may operate as if they were operating in a cloud computing environment, despite the fact they are operating on one or more local device(s) (one or more edge devices) as a single instance or as part of a distributed service that may have no or intermittent public network access to a cloud computing environment associated with the customer. A "region" refers to a geographic location at which a service center resides. A "realm" refers to a logical collection of regions. Realms may be isolated from each other and do not share data.

In some embodiments, the edge device 500 may provide any suitable number of virtual networks (e.g., PVN(s) 505) using compute, memory, and networking resources (e.g., virtual network interface card(s) (VNIC(s) 506)). A virtual network is a logical network that runs on top of a physical substrate network. Using the service(s) 502, one or more customer resources or workloads, such as virtual machines (e.g., virtual machine(s) (VM(s)) 508, executing a compute instance) can be deployed on these private virtual networks. Any suitable combination of VM(s) 508 can execute functionality (e.g., a compute instance, storage, etc.) which is individually accessible through a virtual NIC (e.g., one of the virtual NIC(s) 506). Each VM that is part of a PVN is associated with a VNIC that enables the VM (e.g., a compute instance) to become a member of a subnet of the PVN. The VNIC associated with a VM facilitates the communication of packets or frames to and from the VM. A VNIC can be associated with a VM when the VM is created. PVN(s) 505 can take on many forms, including peer-to-peer networks, IP networks, and others. In some embodiments, substrate network traffic of the service(s) 502 may be encrypted and/or isolated (e.g., by virtue of different PVNs or subnets) from network traffic of one or more the VM(s) 508 executing on the edge device 500.

The edge device 500 thus provides infrastructure and a set of complementary services that enable customers to build and run a wide range of applications (e.g., compute instances), services, and/or storage in a highly available, physically local, and virtual hosted environment. The customer does not manage or control the underlying physical resources provided by the edge device 500 but has control over expanding or reducing virtual machines (e.g., compute instances, virtual NICs, block or object storage, etc.), deploying applications to those virtual machines, and the like. All workloads on the edge device 500 may be split into different CPU sets (e.g., VM and non-VM). One set (e.g., non-VM such as workloads performed by the service(s) 502) may utilize a subset of CPU cores (e.g., 8) of the edge device 500, while the other set (e.g., VM workloads performed by the VM(s) 508) may utilize a different subset of CPU cores.

The edge device 500 may be communicatively connected to a user device (e.g., the computing device 202 of FIG. 2) via one or more network interfaces (e.g., NIC2 and/or NIC 4) and network 520 to interact and/or manage the VM(s) 508. In certain embodiments, a lightweight console can be provided at the user device via a web-based user interface that can be used to access and manage the edge device 500. In some implementations, the console is a web-based application (e.g., one of the service(s) 502) provided by the edge device 500.

FIG. 5 depicts a single edge device. However, it should be appreciated that more than one edge device may be utilized as a distributed computing cluster.

Figure 6:
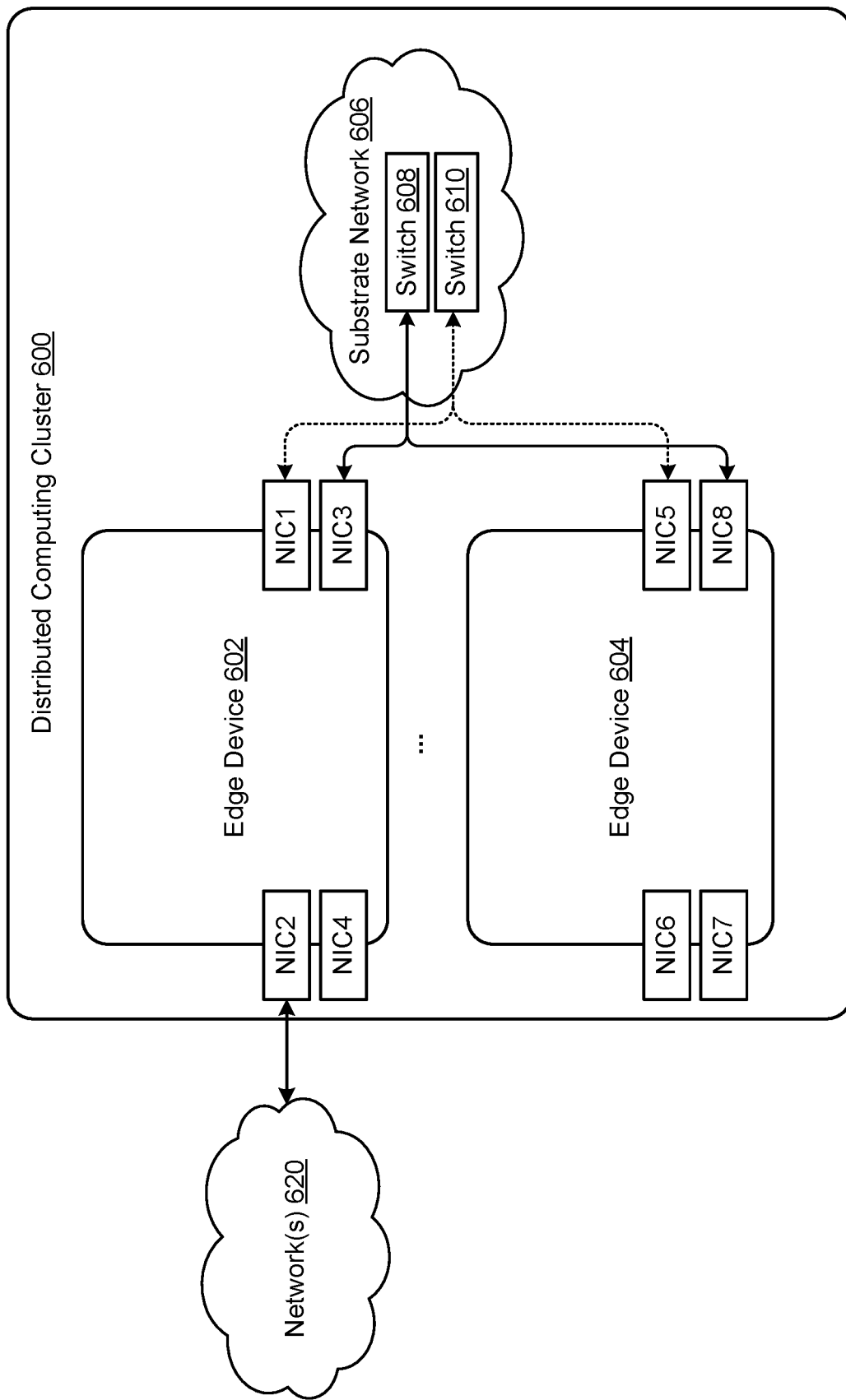
FIG. 6 is a block diagram depicting a distributed computing cluster that includes one or more edge computing devices, according to at least one embodiment.

FIG. 6 is a block diagram depicting a distributed computing cluster 600 that includes one or more edge computing devices (e.g., edge device 602 and 604, each an example of the edge device 500 of FIG. 5), according to at least one embodiment.

Each edge device of the distributed computing cluster 600 may be connected via substrate network 606 (an example of the substrate network 504 of FIG. 5. In some embodiments, the edge devices of the distributed computing cluster 600 (sometimes referred to as "edge computing nodes" or "edge nodes") may be connected by the substrate network 606 using one or more switches (e.g., switch 608 and/or 610). In some embodiments, NIC1 and NIC5 may include a particular connector (e.g., RJ45 connector) while NIC3 and NIC8 may include the same or a different connector (e.g., a QSFP28 100 GbE connector). In some embodiments, only one edge device of the distributed computing cluster 600 is connected to a customer network such as network(s) 620 (an example of the network 520 of FIG. 5). Thus, not only may traffic between services of an edge device be encrypted and isolated from other traffic of a given edge device, but traffic between distributed services operating across multiple edge devices may also be encrypted and isolated from other traffic of the computing cluster. In some embodiments, each edge device is preconfigured as a particular node in the distributed computing cluster 600. In other embodiments, the user can configured the number and topology of the edge devices of the distributed computing cluster 600.

Figure 7:
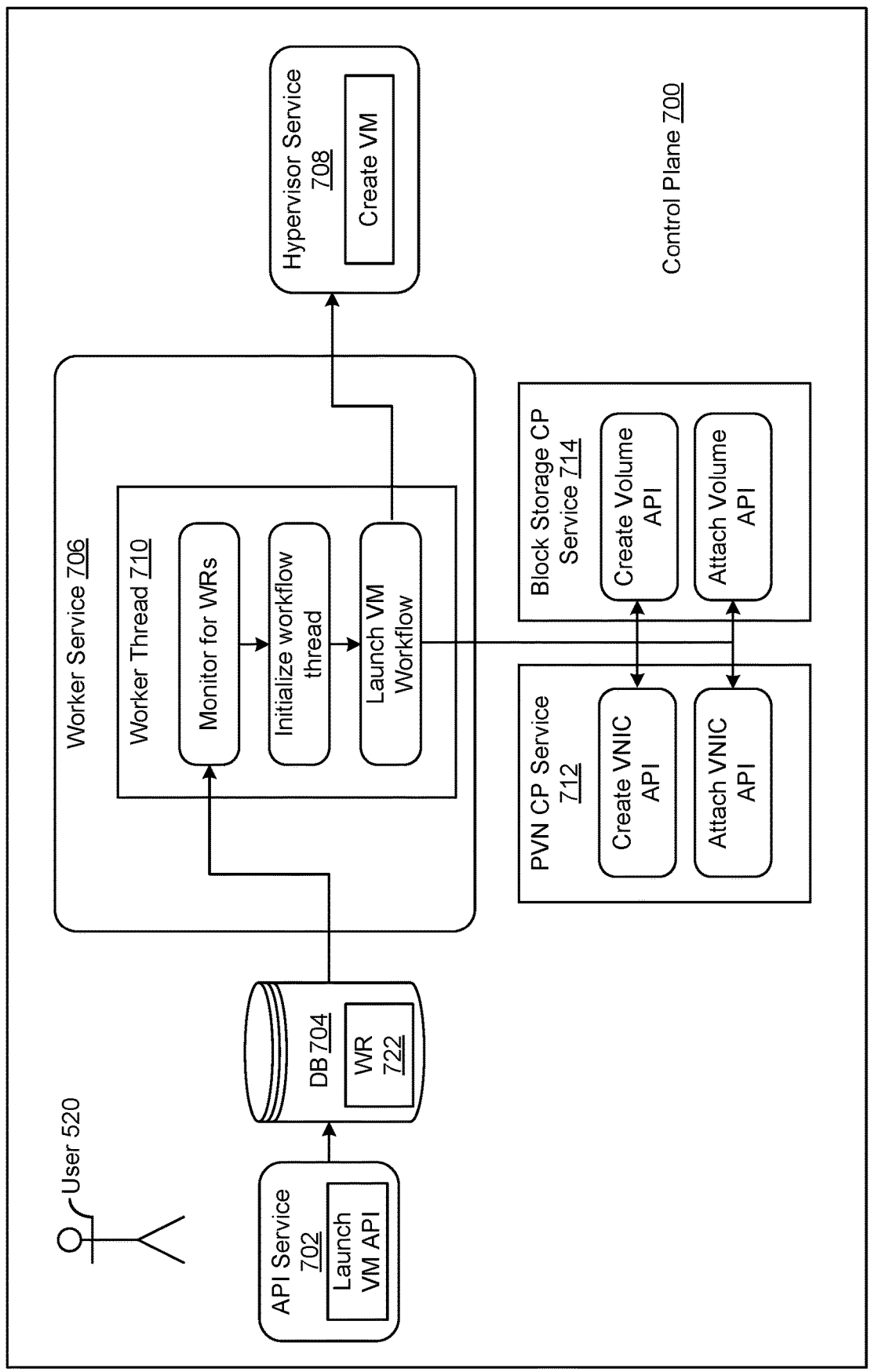
FIG. 7 is a block diagram depicting a flow for executing a workflow by one or more components of a cloud infrastructure edge computing device, according to at least one embodiment.

FIG. 7 is a block diagram depicting a flow 700 for executing a workflow by one or more components of a cloud infrastructure edge computing device, according to at least one embodiment. Components that execute the flow 700 may include API service 702, database (DB) 704, worker service 706, hypervisor service 708, PVN CP service, Block storage CP service 714, although more or fewer services may be included. In some embodiments, each of the services of FIG. 7 are an example of a service of the service(s) 502 of FIG. 5. In some embodiments, at least some of the functionality discussed in connection with the services of FIG. 7 may be combined in any suitable combination and provided as a single service or instances of the same service. By way of example, in some embodiments, the functionality of services 702-708 may be provided by a single service (e.g., compute CP service discussed above in connection with FIG. 5). In some embodiments, the functionality provided by the services 702-708 may be provided by a single edge device (e.g., edge device 500 of FIG. 5) or by two or more edge devices (e.g., by edge device 602 and edge device 604 of FIG. 6).

In some embodiments, the API service 702 may be configured to accept work requests that include intended state data that describes an intended state of a set of data plane resources (e.g., VM(s) 508 of FIG. 5). As a non-limiting example, user 720 may utilize a user device (e.g., the user device *202 of FIG. *2) to access a user interface with which he can make various selections indicating a desire to launch a VM. The user input may be received by the API service 702 (an example of the compute CP service of FIG. 5) which may generate a work request (WR) (e.g., WR 722) and utilize a predefined Launch VM API to store the work request in a distributed database (e.g., DB 704). In some embodiments, the DB 704 may be a computing cluster, which is configured to use etcd3 as an immediately consistent, highly-available, transactional, distributed database. Generally, a work request indicates a desire and information needed to create and/or modify data plane resources such as VM(s) 508. In some embodiments, the work request includes state information indicating a desired state for the data plane resource. In some embodiments, the DB 704 may be accessible to all services operating on any edge device (and by services operating on any suitable edge device of an edge device cluster such as distributed computing cluster 600).

Worker service 706 (e.g., an example of the compute CP service of FIG. 5) may be configured to execute one or more worker processes (e.g., one or more computing threads, such as computing thread 710). Some of these worker processes may be configured by the worker service 706 at any suitable time to execute a continuous and/or ongoing predefined workflow. By way of example, the worker service 706 may configure one or more worker threads (e.g., including computing thread 710) to monitor the DB 704 for new work requests (e.g., WR 722). The computing thread may be configured to determine if a work request WR 722 is already being attended to. In some embodiments, this entails checking a predefined storage bucket within DB 704 for a unique identifier associated with WR 722. If the unique ID included within WR 722 does not appear in the bucket (or the WR is otherwise indicated as having not been picked up for processing), the computing thread 710 (e.g., a nanny thread) may initialize a workflow thread (e.g., another instance of a computing thread 710) which may then be configured by the computing thread 710 to execute a workflow corresponding to launching a VM corresponding to the WR 722.

The initialized workflow thread may be communicatively coupled (e.g., via the substrate network 504 of FIG. 5) to a workflow service (not depicted). The workflow service may be configured to identify, from one or more predefined workflows, a predefined workflow that corresponds to launching a VM, and therefore, to the WR 722. These predefined workflows identify one or more steps/operations to be taken, and a sequence to those steps, in order to achieve a predefined goal (e.g., launching a virtual machine, stopping/starting a virtual machine, terminating a virtual machine, creating a block volume, removing a block volume, etc.). The workflow thread may launch the VM workflow and oversee its execution by various other entities. In some embodiments, the workflow thread may pass any suitable portion of the intended state data of the DP resource to any suitable combination of services.

As a non-limiting example, as part of the workflow for launching a virtual machine (e.g., a VM to be hosted by hypervisor service 708), one or more APIs can be called for creating and attaching the VNIC. Similarly, a number of APIs may be provided for creating and/or attaching a block storage volume API. In some embodiments, the workflow thread may perform any suitable call to one or more APIs to invoke the functionality of PVN CP Service 712, which in turn may be configured to create and attach a VNIC. The workflow thread may then call block storage CP service 714 which may then execute any suitable operations to create and attach a block storage volume. The worker thread overseeing the workflow may ensure a designated order (e.g., create the VNIC first before creating the block volume). This worker thread may be configured to catch any errors and/or exceptions from one or more services it has invoked. If no exceptions/errors are encountered, the worker thread overseeing the workflow can provide any suitable data to the hypervisor service 708 (via the substrate network), which in turn, execute functionality for creating the VM requested. The hypervisor service 708 may provide actual state data for the newly launched VM. In some embodiments, the worker thread overseeing the workflow can store the actual state data in the DB 704 for later reference (e.g., when a monitor may determine whether the actual state data matches the requested state data indicating no changes needed or when the actual state data fails to match the requested state data, indicating a change of the data plane resources is needed).

In some embodiments, the workflow thread may be communicatively coupled to a cluster manager (not depicted). Cluster manager may be configured to manage any suitable number of computing clusters. In some embodiments, the cluster manager may be configured to manage any suitable type of computing cluster (e.g., a Kubernetes cluster, a set of computing nodes used to execute containerized applications, etc.). The workflow thread may be configured to execute any suitable operations to cause the cluster manager to execute any suitable orchestration operation on the DP resource(s) (e.g., a VM) in accordance with the instructions identified to bring the DP resource(s) in line with the intended state data. In some embodiments, a monitoring entity (e.g., the workflow thread, a thread launched by the workflow thread) may be communicatively coupled to DP resource(s) 116 and configured to monitor the health of DP resource(s). In some embodiments, the monitoring entity may be configured to store any suitable health data in the DB 704.

The specific operations and services discussed in connection with FIG. 7 is illustrative in nature and is not intended to limit the scope of this disclosure. The particular operations performed and services utilized may vary depending on the particular workflow associated with the requested operations.

Figure 8:
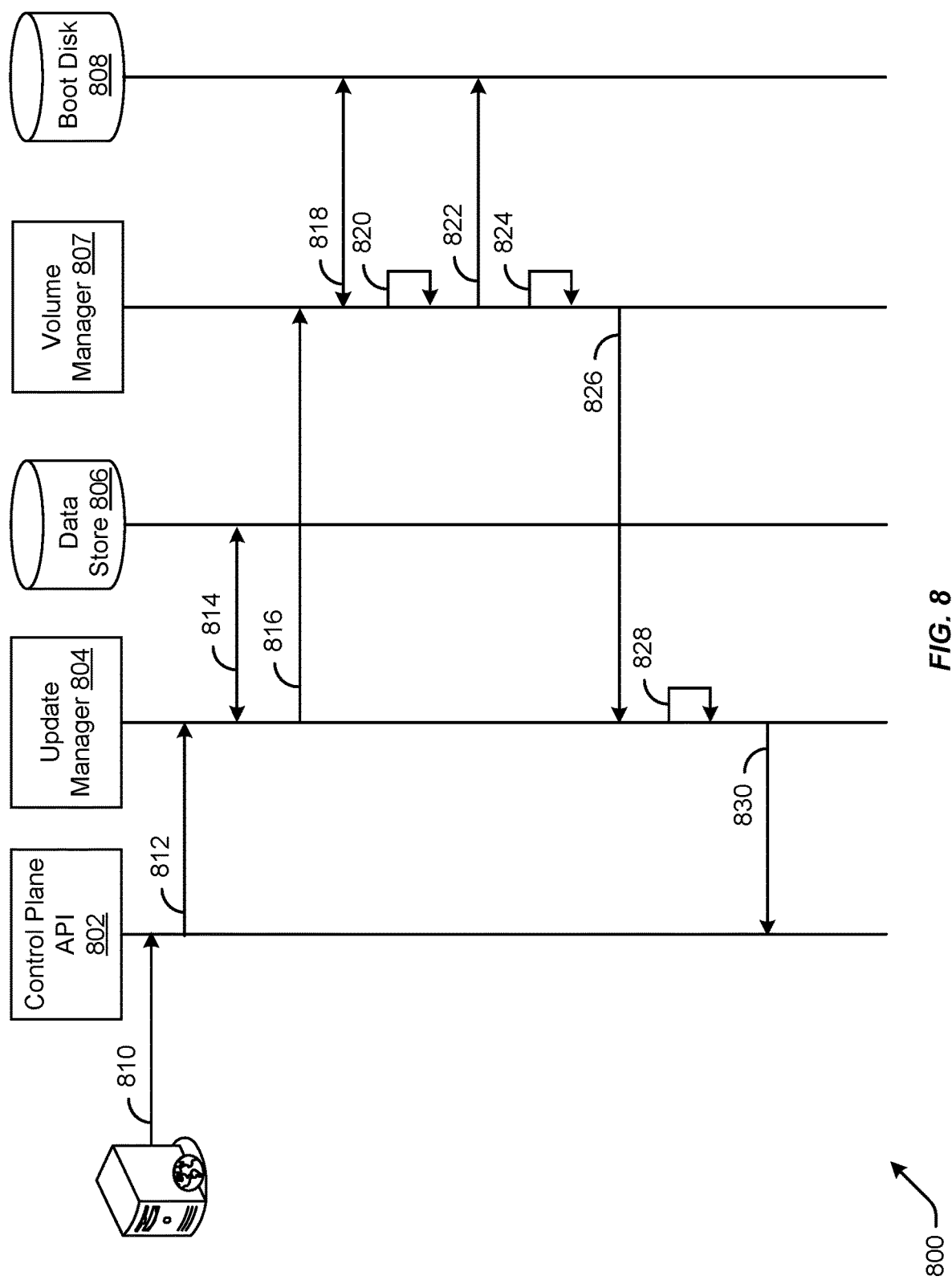
FIG. 8 is a flow diagram for depicting an example method for updating an edge computing device, according to at least one embodiment.

FIG. 8 is a flow diagram for depicting an example method 800 for updating an edge computing device, according to at least one embodiment. Prior to the performance of method 800, the edge computing device (e.g., the edge 500 of FIG. 5) may execute an operating system (OS) corresponding to an OS image with which it has previously been configured. The edge computing device may further execute a set of services corresponding to Docker containers with which the edge computing device has previously been configured. The method 800 may be performed at any suitable time, at any suitable location.

The operations of method 800 may be executed by the control plane API 802 (an example of one of the service(s) 502 of FIG. 5, service API 702 of FIG. 7, etc.), update manager 804 (an example of another service of the service(s) 502), data store 806 (a data store located at the edge device, a remote data store located in a cloud computing environment with which the edge device is communicatively connected, etc.), volume manager 807, and boot disk 808.

In some embodiments, the method 800 may begin at 802, where a request to execute a system update is received by the control plane API 802. The request may be received from computing device 810. Computing device 810 may be an example of a cloud computing device of a cloud computing environment (e.g., a device running an update manager in the cloud). As another example, computing device 810 may be an example of the user device 202 of FIG. 2. In some embodiments, the request is received from a cloud computing environment when the edge computing device is communicatively connected to the cloud computing environment. In some embodiments, the request is received from a user device when the edge computing device is executing within an isolated computing environment having no access to a public network (e.g., the Internet).

In some embodiments, the request may include a manifest. A manifest may be a file that includes data that specifies the configuration of one or more edge devices (e.g., a cluster of edge devices). The manifest may define, for each edge device, any suitable combination of an operating system, a set of services to be executed at the edge device, an identifier for the edge device, networking information (e.g., any suitable information pertaining to one or more network interface cards such as media access control addresses or other suitable identifiers), any suitable attribute of a cluster, cluster node/edge device, or the like.

In some embodiments, the request may include an OS image and/or one or more containers (e.g., Docker containers, etc.) and/or images corresponding to one or more services. In some embodiments, the OS image may include the one or more containers and/or images. Thus, in some embodiments, a request can correspond to an update of the operating system, an update to the services running at the edge computing device, or any suitable combination of the two.

At 812, the request and/or the content of the request (e.g., the OS image, Docker containers, images, etc.) may be provided to update manager 804. In some embodiments, update manager 804 may be configured to manage updating the edge device according to the request. In some embodiments, update manager 804 may operate as a part of volume manager 807.

At 814, if not included in the information provided at 812, the update manager 804 may be configured to obtain the OS image and/or the one or more containers and/or images corresponding to the one or more services from data store 806. In some embodiments, the data store 806 is located in local memory at the edge device and the OS image and/or containers and/or images have been previously copied to the data store 806. In other embodiments, the data store 806 may reside in the cloud computing environment.

At 816, the update manager 804 may provide the OS image, containers, and/or images obtained at 814 to the volume manager 807. In some embodiments, the volume manager 807 may be a copy-on-write file system manager (e.g., B-tree file system (Btrfs), or another suitable file system manager that implements a copy-on-write protocol). In some embodiments, the volume manager may create a new volume snapshot of the current file system (e.g., implemented by an existing volume snapshot that implements the current version of the OS, applications, and/or services with which the edge device is set to boot) to obtain references to all the files of the current file system. The volume manager 807 may be configured to implement any changes to the file system as a modification of the new volume snapshot, rather than modifying the actual files. This process can be referred to as "cloning" in which the volume manager 807 creates a copy-on-write snapshot of each element (e.g., file, directory, etc.) in the file system. Each file and/or directory of the file system can be described by a corresponding data structure (e.g., an "inode" data structure in a Unix-style file system). By cloning, the volume manager 807 may not create a new link pointing to an existing data structure (e.g., an existing inode). In some embodiments, a new data structure (e.g., a new inode) may be created that shares the same disk blocks with the original file. The actual data blocks of each file may not be duplicated, but modifications can be made to the cloned versions such that the modifications are not visible in the original file and vice versa. Any suitable number of cloned versions of a file may exist. A file change can be performed in the new volume snapshot by replacing (e.g., in the data structure for that file) a reference to the original file with a reference of a new file.

It should be appreciated that, prior to providing the data at 816, the update manager 804 may be configured to put the edge device in a read-only mode. In some embodiments, this may entail executing a predefined function call or API. While in read-only mode, resource mutations may be disabled. That is, the resources of the edge device (e.g., services, data plane resources such as virtual machines, and the like) may not be mutated/changed. This allows the edge device to remain in a steady state while the update is performed.

At 818, the volume manager 807 may obtain a snapshot of the existing root file system by accessing boot disk 808. The boot disk 808 may be a data store or partition of the edge device that is configured to store any suitable number of root file systems (e.g., root file system volume snapshots). Obtaining a snapshot of the existing root file system is intended to refer to obtaining a point-in-time view of the files stored within the root file system. This point-in-time view may be assigned an identifier with which the point-in-time copy may be referenced. The snapshot (e.g., a Btrfs snapshot) produced by the volume manager 807 may be a sub-volume that shares data and/or metadata with any suitable number of other sub-volumes using the copy-on-write capabilities of the volume manager 807. Due to the copy-on-write aspects, modifications made to one snapshot (e.g., one sub-volume) are not visible to other snapshots/sub-volumes.

Figure 9:
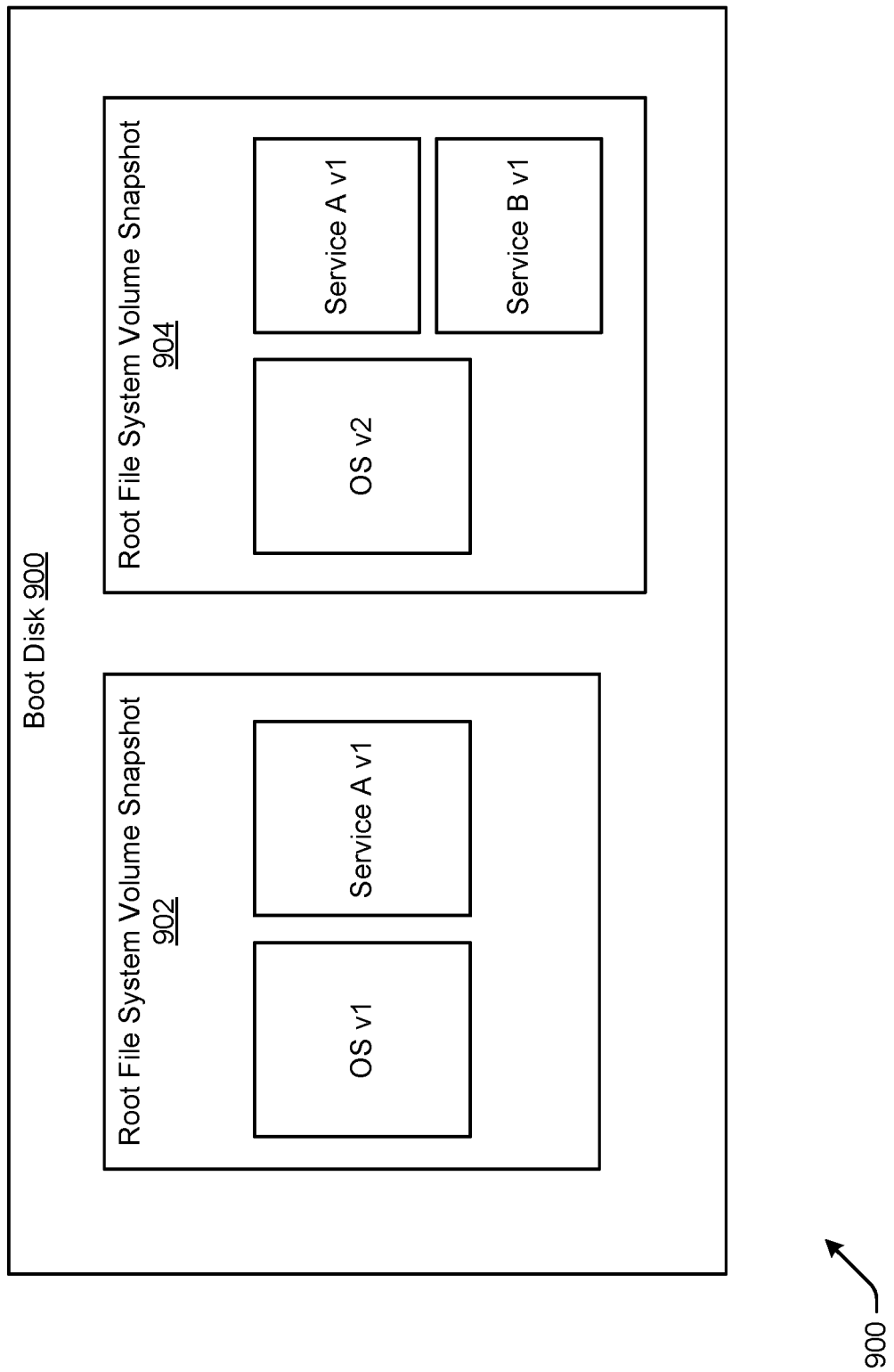
FIG. 9 is a block diagram depicting an example boot disk including at least two root file system volume snapshots, according to at least one embodiment.

FIG. 9 is a block diagram depicting an example boot disk 900 that stores at least two root file system volume snapshots (e.g., root file system volume snapshots 902 and 904 corresponding to two different volumes), according to at least one embodiment. Root file system volume snapshot 902 may store references (and/or data structures such as inode data structures) to any suitable OS image file and/or references to one or more containers (e.g., Docker containers, etc.) and/or references to one or more applications, images corresponding to one or more services, or the like. As depicted in FIG. 9, the root file system volume snapshot 902 may store a snapshot including references to an existing operating system (OS version 1 ("OS v1")) and/or references to images of a set of services with which a device is currently configured (e.g., an image for Service A version 1 ("Service A v1")). Root file system volume snapshot 904 may store references to a different operating system (e.g., OS v2) and/or references to images corresponding to a different set of services (e.g., Service A v1, Service B version 1 ("Service B v1"). One or more of the services referenced in the root file system volume snapshot 904 may be the same as those references in the root file system volume snapshot 902, although one or more of the referenced services may differ. By way of example, root file system volume snapshot 904 may store references to the same image of service A as referenced in root file system volume snapshot 902. Root file system volume snapshot 904 may further include reference to an image for service B that is not referenced in root file system volume snapshot 902. In some embodiments, the edge device can be configured to boot utilizing the data contained in root file system volume snapshot 902 or the data contained in root file system volume snapshot 904. In some embodiments, a user may be provided at startup the choice of booting from either volume snapshot.

Returning to FIG. 8, in some embodiments, the boot disk 808 may be previously (and currently) configured with one root file system volume snapshot (e.g., root file system volume snapshot 902). This root file system volume snapshot may be mounted as the active root file system (e.g., set as the file system within which the edge device will be booted). At 818, the volume manager 807 may obtain a snapshot of root file system volume snapshot 902.

At 820, the volume manager 807 may be configured to compare the snapshot of the currently active root file system (e.g., root file system volume snapshot 902) that comprises references to the current OS image (e.g., OS v1) and/or references to a current set of services (e.g., Service A v1) executing at the edge device to the OS image and/or set of services obtained at 814 (or 812, depending on the use case). If no differences are found by the comparison, the method 800 may end, as the requested update includes no changes to the current file system. Alternatively, although not depicted, if no differences are found, the volume manager 807 can send an indication of the same to the update manager 804 which in turn can provide the computing device 810 an indication that the update was unsuccessful and/or unnecessary. However, if the comparison indicates one or more differences, the method 800 may proceed to 822.

At 822, the volume manager 807 may be configured to create a separate partition within boot disk 808 within which it may store a new root file system volume snapshot (e.g., root file system volume snapshot 904). A partition refers to a section of the boot disk that is separate and isolated from other partitions of the boot disk.

At 824, the volume manager 807 may clone (e.g., make a copy-on-write snapshot) of any suitable portion of the root file system volume snapshot 902 (and/or files referenced by the root file system volume snapshot 902) and any new files may be stored in a portion of the boot disk 808 that is accessible to the root file systems volume snapshots 902 and 904. Root file system volume snapshot 904 may include reference to the files corresponding to OS v2, Service A v1, and Service B v1.

At 826, the volume manager 807 may provide an indication that the requested update has been applied. In some embodiments, the volume manager 807 may provide any suitable identifier and/or location of the updated file system volume snapshot (e.g., root file system volume snapshot 904).

At 828, in response to receiving such an indication, the update manager 804 may be configured to execute any suitable operations to update the default location from which the edge device is booted. By way of example, the update manager 804 may update (or may instruct volume manager 807 to update) the default location from which the edge device is to be booted to a location corresponding to the root file system volume snapshot 904. As another example, the update manager may mount (or may instruct volume manager 807 to mount) the root file system volume snapshot 904 as the default sub-volume from which the edge device will be booted. In some embodiments, the update manager 804 (or volume manager 807) may execute any suitable operations to update a boot order to indicate that the edge device is first to boot from the updated file system volume snapshot (e.g., root file system volume snapshot 904). Although depicted at 828, these operations may be performed at any suitable time (e.g., subsequent to the operations at 824 but before the operations at 826).

At 830, the update manager 804 may send data indicating that the update was successful through the control plane API 802 to the computing device 810.

In some embodiments, both root file system volume snapshots may be available for a period of time (e.g., for 24 hours, for 1 week, for a configurable period of time, or the like) or until user input is received indicating root file system volume snapshot 902 is no longer needed, at which time, root file system volume snapshot 902 may be deleted. In some embodiments, the rollback option is automatically executed when an indication (e.g., user input) that the second operating system is approved has not been received within a threshold period of time (e.g., one hour, 24 hours, etc.) since the second operating system has been in use. In some embodiments, the user of the edge device can select which file system volume snapshot to use each time the device is rebooted. In some embodiments, some aspect of the updated root file system volume snapshot may be faulty or otherwise undesirable. Thus, utilizing the techniques described herein enables the user to roll back to a previous version of the operating system (e.g., using root file system volume snapshot 902) at any suitable time.

Figure 10:
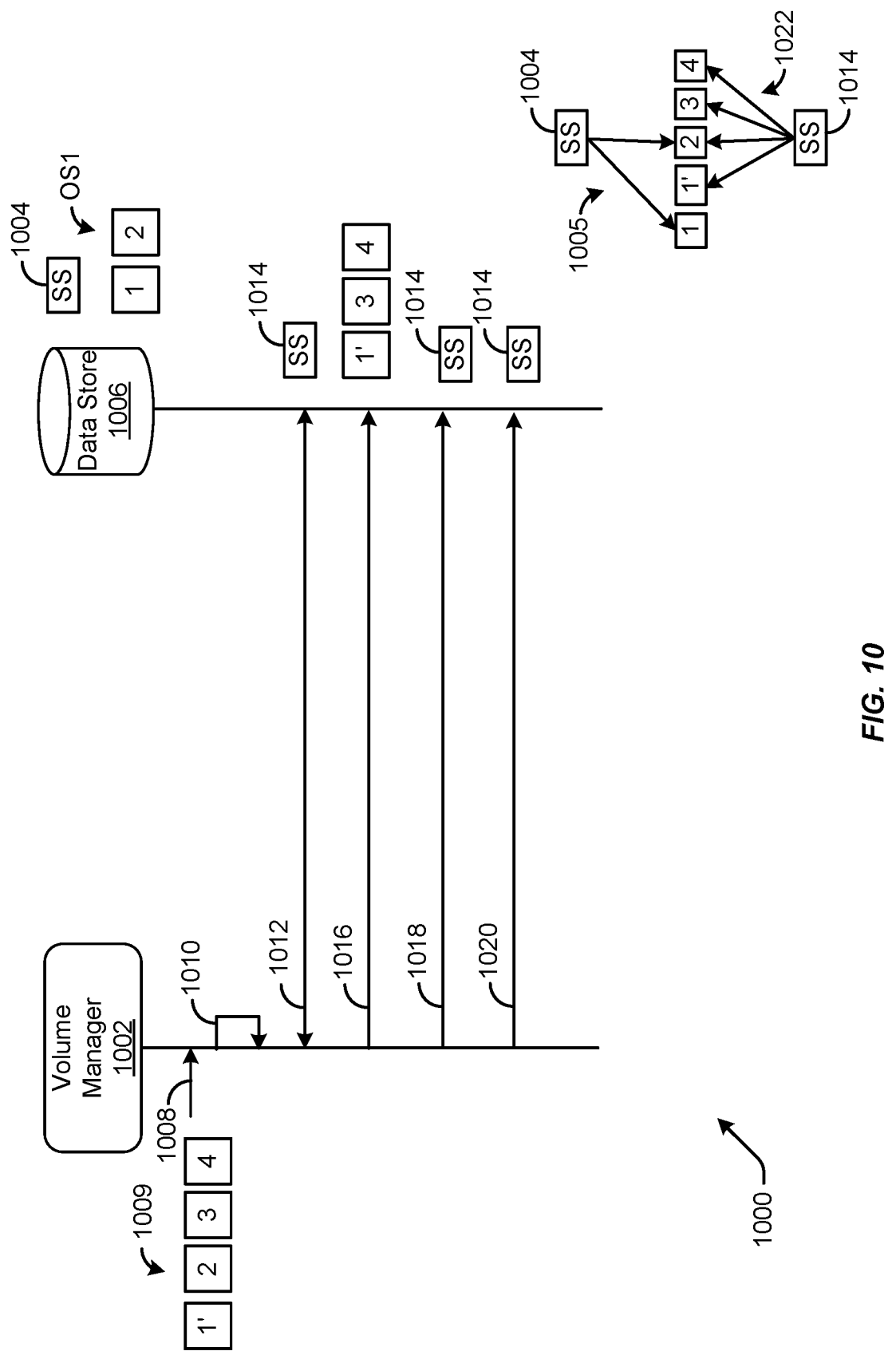
FIG. 10 illustrates an example method for performing a first update of an edge device, in accordance with at least one embodiment.

FIG. 10 illustrates an example method 1000 for performing a first update of an edge device, in accordance with at least one embodiment. Prior to executing the operations of method 1000, the edge device on which volume manager 1002 operates may be configured with a current operating system and an update request to update the device to a different operating system may be received. In the example provided herein, the current operating system (referred to as "OS1") may correspond to files 1 and 2 and a requested operating system (e.g., "OS2," corresponding to a received request to update the edge device to a different operating system) may correspond to the files 1', 2, 3, and 4. File 1' may be a different version of file 1. Snapshot 1004 may previously exist and may include snapshots of (e.g., references to) files 1 and 2 stored in data store 1006. These references are depicted at 1005. Data store 1006 may be part of boot disk 808 of FIG. 8. Prior to execution of method 1000, snapshot 1004 (e.g., a volume generated by the volume manager 1002) may be mounted or otherwise identified as the active root file system from which a particular edge device is booted. Any of the snapshots discussed in connection with FIG. 10 may be mountable volumes from which an edge device may be booted. In some embodiments, these snapshots/volumes may exist in separate partitions, or the same partition, in memory of the edge device. The method 1000 may be performed by volume manager 1002 (an example of the volume manager 807 of FIG. 8). The operations described in connection with method 1000 may be performed in any suitable order, not necessarily the exact order described below.

The method 1000 may begin at 1008, where volume manager 1002 receives a request to update the edge device to OS2 (associated with files 1', 2, 3, and 4 as depicted at 1009). In some embodiments, the request may include a manifest that identifies the files 1', 2, 3, and 4. Any suitable portion of files 1', 2, 3, and 4 may be previously stored at data store 1006 and/or may be included in the request received at 1008.

At 1010, the volume manager 1002 may compare the files associated with snapshot 1004 (corresponding to OS1) to the files associated with OS2. This comparison may indicate that OS1 and OS2 share a common file (e.g., file 2), and that OS2 additionally includes files 1', 3, and 4. If no differences between OS1 and OS2 were found, the volume manager 1002 may be configured to respond to the request indicating the same and/or to cease further execution of the operations of method 1000.

At 1012, the volume manager 1002 may create a snapshot of the data associated with snapshot 1004. That is, the volume manager 1002 may clone snapshot 1004 to create snapshot 1014 (e.g., a copy-on-write version of snapshot 1004). Snapshot 1014 may be stored in data store 1006 and may include references to the same data blocks of files 1 and 2 to which reference of snapshot 1004 refer.

At 1016, and as a result of identifying a difference at 1012, the volume manager 1002 may store files 1', 3, and 4 in data store 1006 (if files, as in this example, files 1', 3, and 4 were not already stored in data store 1006). Data store 1006 may be any suitable memory of the edge device that is accessible by any suitable snapshot of the edge device (e.g., snapshots 1004 and 1014). The data store 1006, snapshot 1004, and snapshot 1014 may all reside in memory of the edge device (e.g., disk memory, boot disk 808 of FIG. 8, etc.).

At 1018, the volume manager 1002 may update snapshot 1014 to replace the original reference to file 1 with a reference to file 1'. Each of snapshots 1004 and 1014 include a snapshot of the file 2 (e.g., a copy-on-write version of the file 2 that is modifiable, yet not visible to the other snapshot).

At 1020, the volume manager 1002 may update the snapshot 1014 with references to files 3 and 4. The resulting references of snapshot 1014 are depicted at 1022.

Unlike conventional systems in which the entire operating system is stored on each root file system, utilizing method 1000 provides a single copy of each file with common files being shared between root file systems to reduce the amount of memory needed to maintain multiple operating systems on the same device. Any suitable number of operating systems may be stored in this manner such that a single copy of each data resource (e.g., each file, or each version of a file such as file 1 and file 1') may be maintained.

Although the example provided in FIG. 10 utilizes operating systems as an example use case, it should be appreciated that the same techniques may be applied to a set of services, a set of virtual machines, files, directories, or the like stored in local memory at the edge device.

Figure 11:
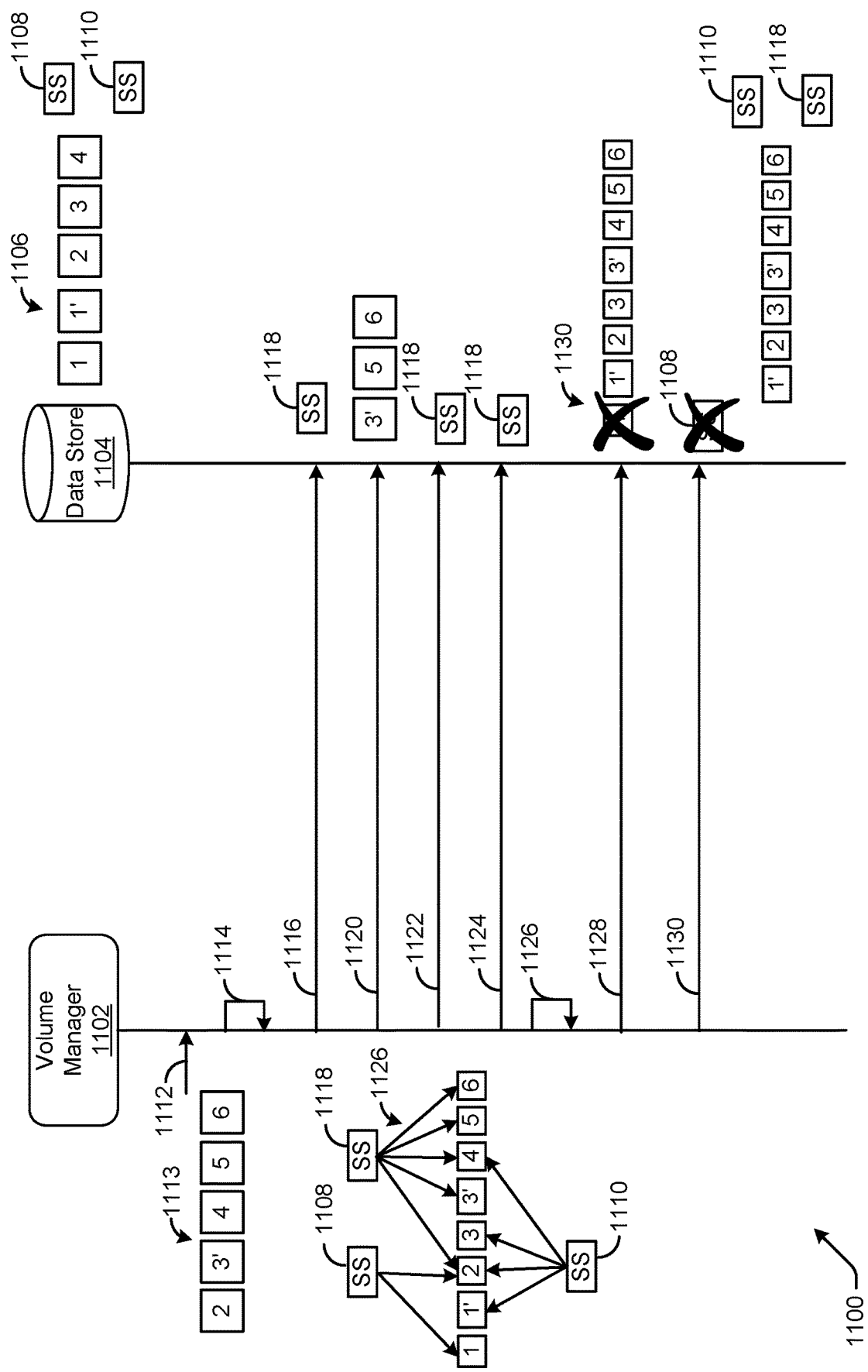
FIG. 11 illustrates an example method for performing a second update of an edge device, in accordance with at least one embodiment.

FIG. 11 illustrates another example method 1100 for performing a second update of an edge device, in accordance with at least one embodiment. Prior to execution of method 1100, data store 1104 (e.g., data store 1006 of FIG. 10, any suitable local memory of an edge device such as the edge device 500 of FIG. 5, etc.) may store files 1106 (e.g., files 1, 1', 2, 3, and 4), snapshot 1108 (e.g., snapshot 1004 of FIG. 10), and snapshot 1110 (e.g., snapshot 1014 of FIG. 10). Any of the snapshots discussed in connection with FIG. 11 may be mountable volumes from which the edge device may be booted. Snapshot 1110 may be currently identified as a default volume from which the edge device boots.

Continuing with the example provided in FIG. 10, the method 1100 may begin at 1112, where volume manager 1102 (an example of the volume manager 1002 of FIG. 10)

may receive a request to update the edge device. The request may include and/or reference files for a new operating system and/or one or more service images. For example, the request may include files 2, 3', 4, 5 and 6 as depicted at 1113. In some embodiments, the request received at 1112 may include a manifest that identifies files 2, 3', 4, 5 and 6 corresponding to the new operating system and/or one or more services.

At 1114, the volume manager 1102 may compare the set of files associated with a default snapshot (e.g., snapshot 1110, the snapshot from which the edge device currently boots, the currently mounted snapshot) to the files associated with the request (e.g., files 2, 3', 4, 5, and 6). At least one of files 5 and 6 may be image containers (e.g., Docker containers) corresponding to respective services. The comparison may indicate that files 2 and 4 are common between snapshot 1110 and the requested update and that the requested update additionally includes/refers to files 3' (a different version of file 3), 5, and 6.

At 1116, the volume manager 1102 may create a snapshot of the data associated with snapshot 1110. That is, the volume manager 1102 may clone snapshot 1110 to create snapshot 1118 (e.g., a copy-on-write version of snapshot 1110). Snapshot 1118 may be stored in data store 1104 and may initially include references to the same data blocks of files 1', 2, 3, and 4 to which references of snapshot 1110 refer.

At 1120, the volume manager 1102 may store files 3', 5, and 6 in data store 1006 (if files 3', 5, and 6 were not already stored in data store 1104).

At 1122, the volume manager 1102 may update snapshot 1118 to replace the original reference to file 3 with a reference to file 3'. Each of snapshots 1110 and 1118 include a snapshot of the files 2 and 4 (e.g., a copy-on-write version of the files 2 and 4 that are modifiable, yet not visible to the other snapshot).

At 1124, the volume manager 1102 may update the snapshot 1118 with references to files 5 and 6. The resulting references of snapshot 1118 are depicted at 1126.

In some embodiments, the volume manager 1102 may be configured to manage any suitable number of root file systems. However, in other embodiments, the volume manager 1102 may be configured to manage a limited number of root file systems (e.g., two root file systems). In accordance with these embodiments, the volume manager 1102, upon identifying that the number of root file systems has exceeded the limit, may execute any suitable operations for reducing the number of root file systems to a number that no longer exceeds the limit.

For example, at 1126, the volume manager 1102 may execute operations to identify a root file system to delete. In some embodiments, each root file system (corresponding to snapshots 1108, 1110, and 1118, separate volumes previously created by the volume manager 1102) may be associated with an identifier (e.g., a timestamp, a name, a creation date, etc.) that indicates a time at which the root file system (e.g., snapshot) was created. In some embodiments, the volume manager 1102 may be configured to select an oldest root file system for deletion. Alternatively, user input may be prompted at any suitable time to select a root file system for deletion. In some embodiments, any suitable predefined rules for selecting a root file system for deletion may be utilized. As a non-limiting example, the volume manager 1102 may select the root file system corresponding to snapshot 1108 for deletion.

At 1128, the volume manager 1102 may identify one or more files for deletion and execute corresponding operations to delete those files from the data store 1104. By way of example, the volume manager 1102 may identify that files 1 and 2 correspond to snapshot 1108. The volume manager 1102 may determine whether any of the files of snapshot 1108 are referenced by any other existing root file system (e.g., snapshots 1110 and/or 1118). By way of example, volume manager 1102 may identify that snapshots 1108 and 1110 both refer to file 2, but that no other root file system utilizes file 1. Upon making this determination, volume manager 1102 may execute instructions to delete file 1 from the set of files stored within data store 1104 as depicted at 1128.

At 1130, the volume manager 1102 may execute any suitable instructions for deleting snapshot 1108. Data store 1104 would then store files 1', 2, 3, 3', 4, 5, and 6, and snapshots 1110 and 1118.

Figure 12:
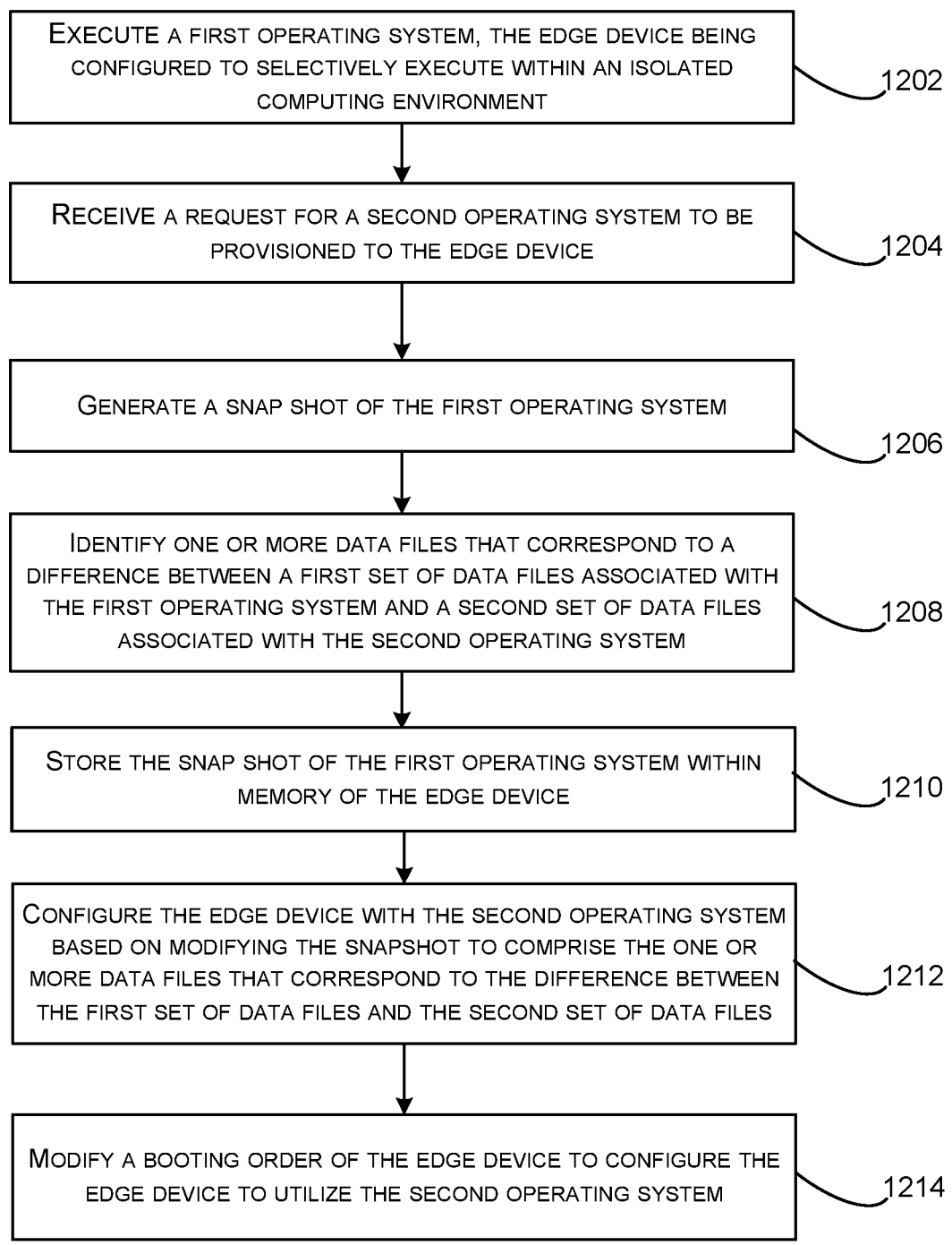
FIG. 12 is a block diagram illustrating another example method for updating an operating system of an edge computing device, in accordance with at least one embodiment.

FIG. 12 is a block diagram illustrating another example method 1200 for updating an edge computing device, in accordance with at least one embodiment. The operations of method 1200 may be performed in any suitable order. Although a particular number of operations are illustrated the method 1200 may include more or fewer operations than those depicted. In some embodiments, the method 1200 may be performed by an edge device (e.g., an edge device running a copy-on-write file manager such as Btrfs, of which volume managers 1002 and 1102 of FIGS. 10 and 11, respectively, are an example). Although FIG. 12 discusses updating an operating system, similar operations may be performed to update any suitable file stored at the edge device.

The method 1200 may begin at 1202, where a first operating system may be executed at an edge device (e.g., the edge device 500 of FIG. 5). In some embodiments, the edge device is configured to selectively execute within an isolated computing environment (e.g., an environment in which no access to a public network is available).

At 1204, a request may be received (e.g., by the update manager 804 of FIG. 8, an example of the service(s) 502 of FIG. 5). The request (e.g., an example of the requests 1008 and/or 1112 of FIGS. 10 and 11, respectively) may identify (e.g., via a manifest included with the request or otherwise) a second operating system to be provisioned to the edge device. For example, one or more files of the second operating system may be identified and/or provided within the request. In some embodiments, the request may include any suitable combination of an OS image, containers (e.g., Docker containers, etc.), software images, or the like. In some embodiments, the request may include an identifier with which such data may be retrieved (e.g., from data store 806 of FIG. 8 if such data had previously been stored in data store 806).

At 1206, a snapshot of the first operating system may be generated. The snapshot may indicate a set of files corresponding to the first operating system at a particular point in time. An example of the snapshot of the first operating system is snapshot 1004 FIG. 10.

At 1208, one or more data files that correspond to a difference between a first set of data files associated with the first operating system and a second set of data files associated with the second operating system may be identified. By way of example, a difference may be identified by comparing the snapshot of the first operating system to the data received (or obtained) as described at 1204.

At 1210 (e.g., when a difference is identified at 1208), a new root file system (e.g., snapshot 1014 of FIG. 10) may be generated (e.g., by the volume manager 1002 of FIG. 10) in local memory.

The snapshot of the first operating system (e.g., snapshot 1014) may be stored within memory (e.g., in data store 1006).

At 1212, the edge device may be configured with the second operating system based on modifying the snapshot to comprise the one or more data files that correspond to the difference between the first set of data files and the second set of data files. The operations performed at 1214 may be similar or the same to the ones corresponding to the operations performed at 1018 and/or 1020 of method 1000 discussed above.

At 1214, a booting order of the edge device may be modified (e.g., by the volume manager) to configure the edge device to utilize the second operating system.

Although specific embodiments have been described, various modifications, alterations, alternative constructions, and equivalents are also encompassed within the scope of the disclosure. Embodiments are not restricted to operation within certain specific data processing environments, but are free to operate within a plurality of data processing environments. Additionally, although embodiments have been described using a particular series of transactions and steps, it should be apparent to those skilled in the art that the scope of the present disclosure is not limited to the described series of transactions and steps. Various features and aspects of the above-described embodiments may be used individually or jointly.

Further, while embodiments have been described using a particular combination of hardware and software, it should be recognized that other combinations of hardware and software are also within the scope of the present disclosure. Embodiments may be implemented only in hardware, or only in software, or using combinations thereof. The various processes described herein can be implemented on the same processor or different processors in any combination. Accordingly, where components or modules are described as being configured to perform certain operations, such configuration can be accomplished, e.g., by designing electronic circuits to perform the operation, by programming programmable electronic circuits (such as microprocessors) to perform the operation, or any combination thereof. Processes can communicate using a variety of techniques including but not limited to conventional techniques for inter process communication, and different pairs of processes may use different techniques, or the same pair of processes may use different techniques at different times.

The specification and drawings are, accordingly, to be regarded in an illustrative rather than a restrictive sense. It will, however, be evident that additions, subtractions, deletions, and other modifications and changes may be made thereunto without departing from the broader spirit and scope as set forth in the claims. Thus, although specific disclosure embodiments have been described, these are not intended to be limiting. Various modifications and equivalents are within the scope of the following claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known for carrying out the disclosure. Variations of those preferred embodiments may become apparent to those of ordinary skill in the art upon reading the foregoing description. Those of ordinary skill should be able to employ such variations as appropriate and the disclosure may be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein.

All references, including publications, patent applications, and patents, cited herein are hereby incorporated by reference to the same extent as if each reference were individually and specifically indicated to be incorporated by reference and were set forth in its entirety herein.

In the foregoing specification, aspects of the disclosure are described with reference to specific embodiments thereof, but those skilled in the art will recognize that the disclosure is not limited thereto. Various features and aspects of the above-described disclosure may be used individually or jointly. Further, embodiments can be utilized in any number of environments and applications beyond those described herein without departing from the broader spirit and scope of the specification. The specification and drawings are, accordingly, to be regarded as illustrative rather than restrictive.

What is claimed is:

1. A computer-implemented method, comprising:
    executing, by an edge device, a first operating system, the edge device being configured to selectively execute within an isolated computing environment;
    receiving, by the edge device, a request for updating the edge device, the request indicating a second operating system to be provisioned to the edge device, and the request comprising a manifest that specifies a set of services to be provisioned at the edge device;
    generating, by the edge device, a snapshot of the first operating system;
    identifying one or more data files that correspond to a difference between a first set of data files associated with the first operating system and a second set of data files associated with the second operating system;

storing the snapshot of the first operating system within memory of the edge device;

configuring the edge device with the second operating system and the set of services specified in the manifest based at least in part on: 1) modifying the snapshot of the first operating system to comprise the one or more data files that correspond to the difference between the first set of data files associated with the first operating system and the second set of data files associated with the second operating system, and 2) maintaining a first indication that a first set of image containers associated with a set of services that were previously provisioned at the edge device is associated with a first configuration of the edge device and a second indication that a second set of image containers associated with the set of services specified by the manifest correspond to a second configuration of the edge device; and modifying a booting order of the edge device to configure the edge device to utilize the second operating system and the set of services specified in the manifest.

2. The computer-implemented method of claim 1, further comprising maintaining data that indicates that the first set of data files correspond to the first operating system and the second set of data files corresponds to the second operating system, wherein at least one data file is common between the first set of data files and the second set of data files.

3. The computer-implemented method of claim 1, the computer-implemented method further comprising:
comparing, by the edge device, the set of services previously provisioned at the edge device to the set of services specified by the manifest;
identifying one or more services that correspond to the difference between the set of services previously provisioned at the edge device and the set of services specified by the manifest;
obtaining one or more image containers corresponding to the one or more identified services; and
executing one or more tasks associated with provisioning the one or more identified services at the edge device in accordance with the manifest, wherein at least one image container is common between the first set of image containers and the second set of image containers.

4. The computer-implemented method of claim 3, wherein local memory of the edge device stores only one instance of a given image container.

5. The computer-implemented method of claim 1, wherein the edge device is configured with a volume manager that implements a copy-on-write protocol.

6. The computer-implemented method of claim 1, further comprising providing a rollback option that enables a user to roll back from the second operating system to the first operating system.

7. The computer-implemented method of claim 6, wherein the rollback option is automatically executed when an indication that the second operating system is approved has not been received within a threshold period of time since the second operating system has been in use.

8. An edge device, comprising:
one or more processors; and
one or more memories configured with computer-executable instructions that, when executed by the one or more processors, cause the edge device to:
execute a first operating system, the edge device being configured to selectively execute within an isolated computing environment;
receive a request for updating the edge device, the request indicating a second operating system to be provisioned to the edge device, and the request comprising a manifest that specifies a set of services to be provisioned at the edge device;
generate a snapshot of the first operating system;
identify one or more data files that correspond to a difference between a first set of data files associated with the first operating system and a second set of data files associated with the second operating system;
store the snapshot of the first operating system within memory of the edge device;
configure the edge device with the second operating system and the set of services specified in the manifest based at least in part on: 1) modifying the snapshot of the first operating system to comprise the one or more data files that correspond to the difference between the first set of data files associated with the first operating system and the second set of data files associated with the second operating system, and 2) maintaining a first indication that a first set of image containers associated with a set of services that were previously provisioned at the edge device is associated with a first configuration of the edge device and a second indication that a second set of image containers associated with the set of services specified by the manifest correspond to a second configuration of the edge device; and
modify a booting order of the edge device to configure the edge device to utilize the second operating system and the set of services specified in the manifest.

9. The edge device of claim 8, wherein executing the instructions further causes the edge device to maintain data that indicates that the first set of data files correspond to the first operating system and the second set of data files corresponds to the second operating system, wherein at least one data file is common between the first set of data files and the second set of data files.

10. The edge device of claim 8, wherein executing the computer-executable instructions further causes the edge device to:
compare the set of services previously provisioned at the edge device to the set of services specified by the manifest;
identify one or more services that correspond to a difference between the set of services previously provisioned at the edge device and the set of services specified by the manifest;
obtain one or more image containers corresponding to the one or more identified services; and
execute one or more tasks associated with provisioning the one or more identified services at the edge device in accordance with the manifest, wherein at least one image container is common between the first set of image containers and the second set of image containers.

11. The edge device of claim 10, wherein the one or more memories store only one instance of a given image container.

12. The edge device of claim 8, wherein the edge device is configured with a volume manager that implements a copy-on-write protocol.

13. The edge device of claim 8, further comprising providing a rollback option that enables a user to roll back from the second operating system to the first operating system.

14. The edge device of claim 13, wherein the rollback option is automatically executed when an indication that the second operating system is approved has not been received within a threshold period of time since the second operating system has been in use.

15. A non-transitory computer-readable storage medium comprising computer-executable instructions that, when executed with one or more processors of an edge device, cause the edge device to:
- execute a first operating system, the edge device being configured to selectively execute within an isolated computing environment;
- receive a request for updating the edge device, the request indicating a second operating system to be provisioned to the edge device, and the request comprising a manifest that specifies a set of services to be provisioned at the edge device;
- generate a snapshot of the first operating system;
- identify one or more data files that correspond to a difference between a first set of data files associated with the first operating system and a second set of data files associated with the second operating system;
- store the snapshot of the first operating system within memory of the edge device;
- configure the edge device with the second operating system and the set of services specified in the manifest based at least in part on: 1) modifying the snapshot of the first operating system to comprise the one or more data files that correspond to the difference between the first set of data files associated with the first operating system and the second set of data files associated with the second operating system, and 2) maintaining a first indication that a first set of image containers associated with a set of services that were previously provisioned at the edge device is associated with a first configuration of the edge device and a second indication that a second set of image containers associated with the set of services specified by the manifest correspond to a second configuration of the edge device; and
- modify a booting order of the edge device to configure the edge device to utilize the second operating system and the set of services specified in the manifest.

16. The non-transitory computer-readable storage medium of claim 15, wherein executing the instructions further causes the edge device to maintain data that indicates that the first set of data files correspond to the first operating system and the second set of data files corresponds to the second operating system, wherein at least one data file is common between the first set of data files and the second set of data files.

17. The non-transitory computer-readable storage medium of claim 15, wherein executing the computer-executable instructions further causes the edge device to:
- compare the set of services previously provisioned at the edge device to the set of services specified by the manifest;
- identify one or more services that correspond to the difference between the set of services previously provisioned at the edge device and the set of services specified by the manifest;
- obtain one or more image containers corresponding to the one or more identified services; and
- execute one or more tasks associated with provisioning the one or more identified services at the edge device in accordance with the manifest, wherein at least one image container is common between the first set of image containers and the second set of image containers.

18. The non-transitory computer-readable storage medium of claim 17, wherein the one or more memories store only one instance of a given image container.

19. The non-transitory computer-readable storage medium of claim 15, wherein the edge device is configured with a volume manager that implements a copy-on-write protocol.

20. The non-transitory computer-readable storage medium of claim 15, further comprising providing a rollback option that enables a user to roll back from the second operating system to the first operating system, the rollback option being automatically executed when an indication that the second operating system is approved has not been received within a threshold period of time since the second operating system has been in use.

* * * * *